United States Patent
Nguyen et al.

(10) Patent No.: US 8,814,883 B2
(45) Date of Patent: *Aug. 26, 2014

(54) MINIMALLY INVASIVE SURGICAL STABILIZATION DEVICES AND METHODS

(75) Inventors: Mimi Nguyen, Redwood City, CA (US); Rosendo Aguilar, Newark, CA (US); Betsy Swann, Grass Valley, CA (US); Elisa Janine Aldridge, Menlo Park, CA (US); Christopher A. Stout, San Mateo, CA (US); Philip Albert Bailey, San Mateo, CA (US)

(73) Assignee: Bayer Essure Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,564

(22) Filed: May 24, 2011

(65) Prior Publication Data
US 2011/0224486 A1  Sep. 15, 2011

Related U.S. Application Data

(60) Continuation of application No. 13/006,247, filed on Jan. 13, 2011, which is a division of application No. 11/165,733, filed on Jun. 24, 2005, now Pat. No. 7,918,863.

(51) Int. Cl.
*A61D 1/06* (2006.01)
*A61F 6/06* (2006.01)
*A61B 1/00* (2006.01)
*A61M 5/178* (2006.01)

(52) U.S. Cl.
USPC ........... 606/135; 128/830; 128/831; 128/833; 128/838; 128/839; 600/104; 604/164.1

(58) Field of Classification Search
USPC ............... 600/101–184; 604/158, 161, 163, 604/167.03, 171, 523, 70, 95.1, 604/167.01–167.04, 164.01–164.09, 198, 604/192, 533–539; 128/830–831, 840; 424/422; 606/28, 108, 135, 151
See application file for complete search history.

(56) References Cited

U.S. PATENT DOCUMENTS

| | | | | |
|---|---|---|---|---|
| 4,027,510 A | * | 6/1977 | Hiltebrandt | 72/37 |
| 4,245,623 A | | 1/1981 | Erb | |
| 4,805,618 A | | 2/1989 | Ueda et al. | |

(Continued)

FOREIGN PATENT DOCUMENTS

| | | |
|---|---|---|
| EP | 0 891 757 A2 | 1/1999 |
| GB | 2 021 956 A | 12/1979 |
| GB | 2 156 224 A | 10/1985 |
| WO | WO 99/15116 | 4/1999 |

OTHER PUBLICATIONS

PCT Invitation to Pay Additional Fees, PCT/US2006/012952, dated mailed Feb. 2, 2007, total 8 pages.

(Continued)

*Primary Examiner* — Patricia Bianco
*Assistant Examiner* — Tarla Patel
(74) *Attorney, Agent, or Firm* — Blakely, Sokoloff, Taylor & Zafman LLP

(57) ABSTRACT

The various embodiments of the present inventions provide stabilization devices and methods for use of the stabilization devices with minimally invasive gynecological procedures such as methods of preventing pregnancy by inserting intrafallopian contraceptive devices into the fallopian tubes.

22 Claims, 30 Drawing Sheets

(56) References Cited

U.S. PATENT DOCUMENTS

| | | | |
|---|---|---|---|
| 5,312,415 A | | 5/1994 | Palermo |
| 5,513,628 A | * | 5/1996 | Coles et al. .............. 128/200.26 |
| 5,741,320 A | * | 4/1998 | Thornton et al. ............. 607/122 |
| 5,743,904 A | | 4/1998 | Edwards |
| 5,749,889 A | | 5/1998 | Bacich et al. |
| 5,935,137 A | | 8/1999 | Saadat et al. |
| 6,162,196 A | | 12/2000 | Hart et al. |
| 6,526,979 B1 | | 3/2003 | Nikolchev et al. |
| 6,634,361 B1 | | 10/2003 | Nikolchev et al. |
| 6,705,323 B1 | | 3/2004 | Nikolchev et al. |
| 6,709,667 B1 | | 3/2004 | Lowe et al. |
| 6,726,682 B2 | | 4/2004 | Harrington |
| 6,740,039 B1 | | 5/2004 | Rafter et al. |
| 6,802,825 B2 | | 10/2004 | Ackerman et al. |
| 6,847,336 B1 | | 1/2005 | Lemelson et al. |
| 6,899,105 B2 | | 5/2005 | Krueger et al. |
| 7,289,139 B2 | | 10/2007 | Amling et al. |
| 7,338,473 B2 | * | 3/2008 | Campbell et al. ......... 604/167.01 |
| 7,398,780 B2 | | 7/2008 | Callister et al. |
| 7,736,371 B2 | | 6/2010 | Schoepp |
| 2002/0049423 A1 | * | 4/2002 | Howell et al. ................ 604/528 |
| 2002/0072744 A1 | | 6/2002 | Harrington |
| 2003/0009128 A1 | | 1/2003 | Ackerman |
| 2003/0051735 A1 | | 3/2003 | Pavcnik et al. |
| 2003/0105473 A1 | | 6/2003 | Miller |
| 2003/0158464 A1 | | 8/2003 | Bertolero |
| 2003/0206099 A1 | | 11/2003 | Richman |
| 2004/0158127 A1 | * | 8/2004 | Okada ........................... 600/127 |
| 2004/0162465 A1 | | 8/2004 | Carrillo |
| 2005/0004512 A1 | | 1/2005 | Campbell et al. |
| 2005/0045184 A1 | | 3/2005 | Khera et al. |
| 2005/0070757 A1 | | 3/2005 | Niwa et al. |
| 2005/0085880 A1 | | 4/2005 | Truckai et al. |
| 2005/0119617 A1 | | 6/2005 | Stecker et al. |
| 2005/0232961 A1 | | 10/2005 | Lowe et al. |
| 2005/0265996 A1 | | 12/2005 | Lentz |
| 2005/0267417 A1 | | 12/2005 | Secrest et al. |
| 2005/0288551 A1 | | 12/2005 | Callister et al. |
| 2006/0116692 A1 | | 6/2006 | Ward |
| 2006/0235433 A1 | * | 10/2006 | Secrest et al. ................. 606/114 |
| 2006/0293560 A1 | | 12/2006 | Nguyen et al. |
| 2007/0088247 A1 | | 4/2007 | Bliweis et al. |
| 2007/0213590 A1 | | 9/2007 | Squicciarini |
| 2008/0041394 A1 | | 2/2008 | Swann et al. |
| 2008/0154256 A1 | | 6/2008 | Payne et al. |
| 2010/0063360 A1 | | 3/2010 | Harrington et al. |
| 2011/0094519 A1 | | 4/2011 | Gopal |

OTHER PUBLICATIONS

PCT Notification of Transmittal of International Search Report and the Written Opinion of the International Searching Authority or the Declaration, PCT/US2006/012952, mail date Apr. 27, 2007, total 18 pages.

PCT Notification Concerning Transmittal of International Preliminary Report on Patentability (Chapter 1 of the Patent Cooperative Treaty), and the PCT Written Opinion of the International Searching Authority PCT/US2006/012952, mail date Jan. 10, 2008, total 12 pages.

* cited by examiner

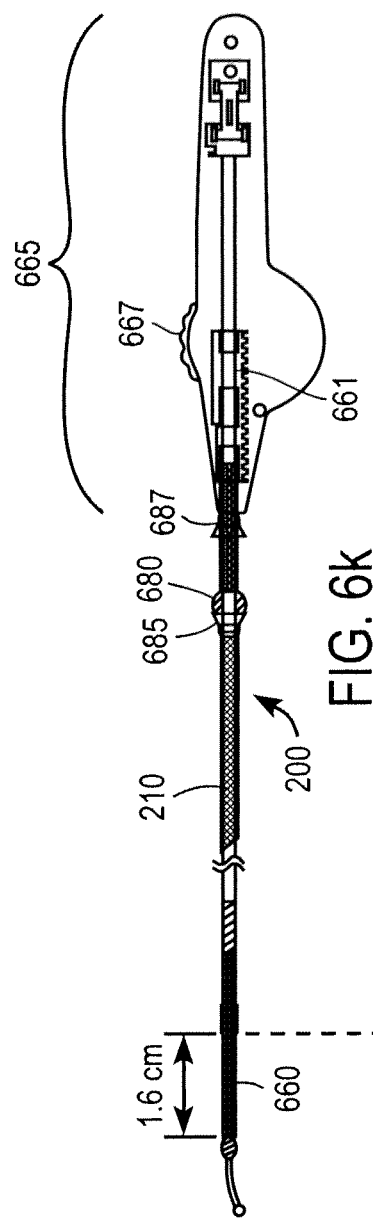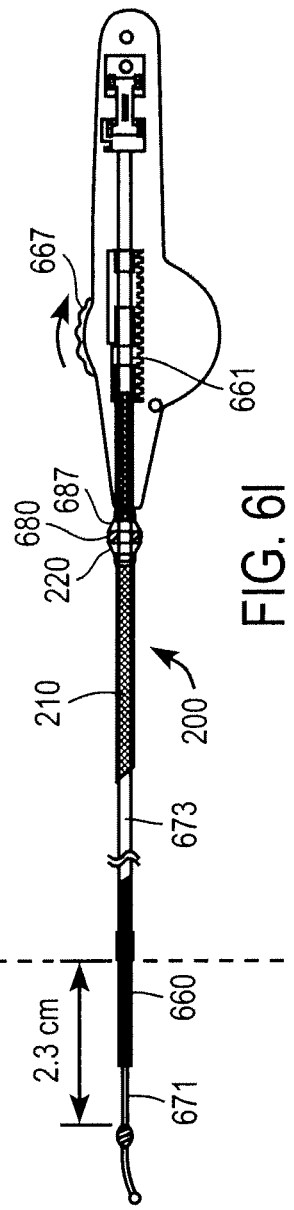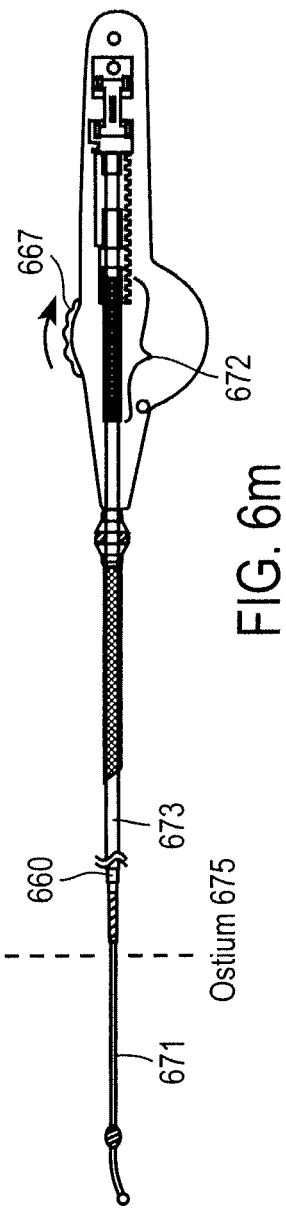

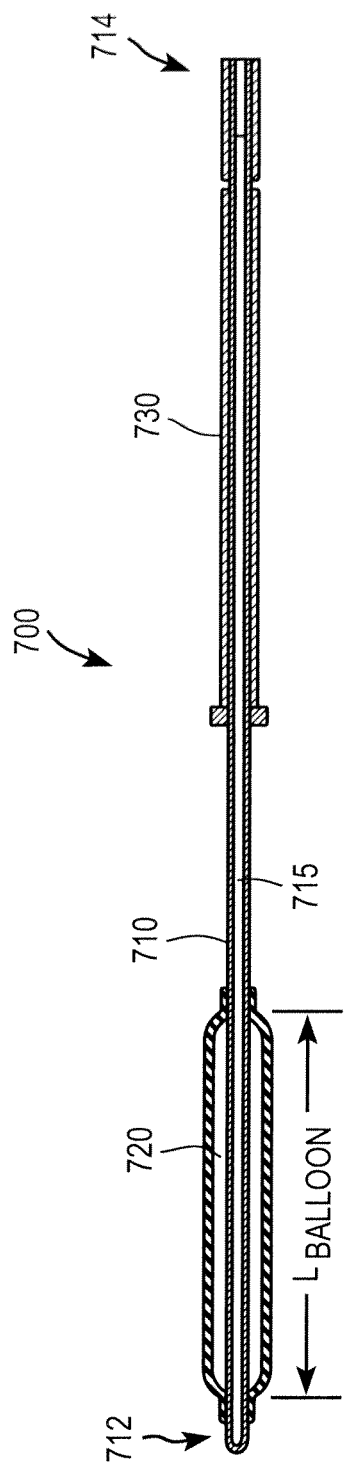
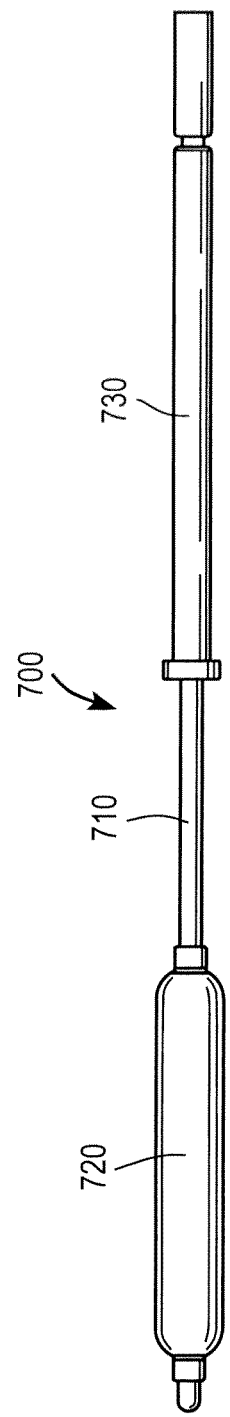
FIG. 7a
FIG. 7b

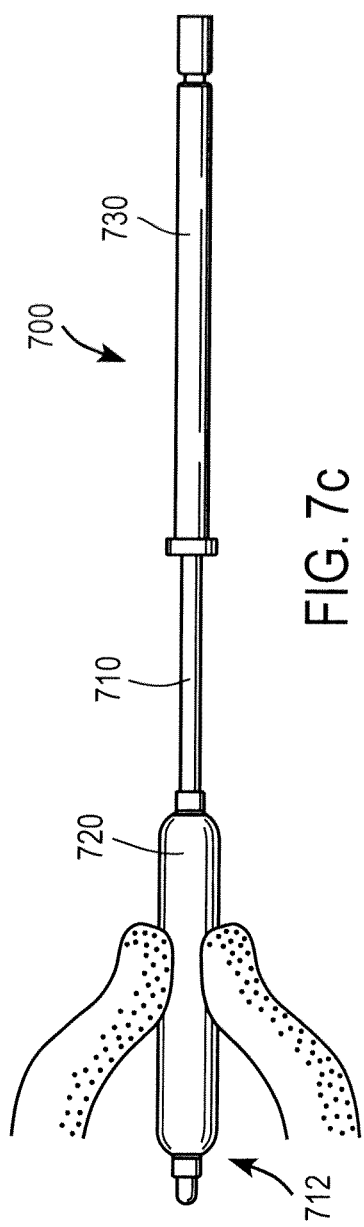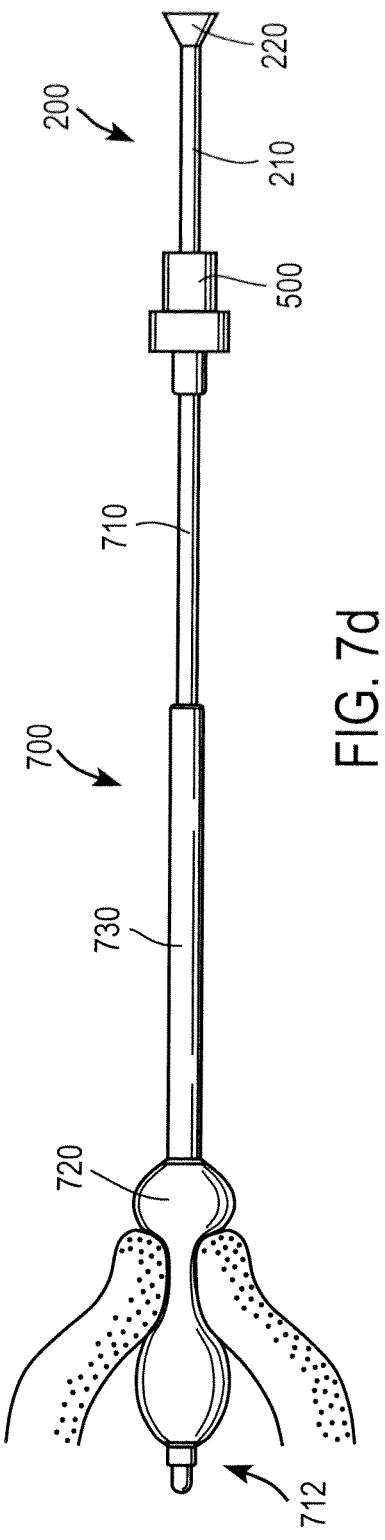
FIG. 7c
FIG. 7d

MINIMALLY INVASIVE SURGICAL STABILIZATION DEVICES AND METHODS

This application is a continuation of U.S. patent application Ser. No. 13/006,247, filed on Jan. 13, 2011, which is a divisional of U.S. patent application Ser. No. 11/165,733, filed on Jun. 24, 2005, now issued as U.S. Pat. No. 7,918,863, which is incorporated herein by reference in its entirety.

BACKGROUND OF THE INVENTION

1. Field of the Invention

The present invention relates to the field of minimally invasive surgical medical devices and medical procedures. More specifically, the invention relates to devices and methods used for transcervical gynecological procedures.

2. Discussion of Related Art

Female contraception and/or sterilization may be affected by transcervically introducing an object (e.g. a coil) into a fallopian tube to inhibit conception. Devices, systems and methods for such a contraceptive approach have been described in various patents and patent applications assigned to the present assignee. For example, PCT Patent Application No. PCT/US98/20031 published as WO 99/15116 and U.S. Pat. No. 6,526,979 and U.S. Pat. No. 6,634,361, and is hereby incorporated herein by reference in its entirety, describe devices that are transcervically inserted into an ostium of a fallopian tube and mechanically anchored within the fallopian tube. The devices described in these patents and patent applications may promote a tissue in-growth around and within the inserted device, which may be referred to as an implant or an insert. One example of such devices is the device known as "Essure" from Conceptus, Inc. of Mountain View, Calif. This tissue in-growth tends to provide long-term contraception and/or permanent sterilization without the need for surgical procedures.

The device used to insert the contraceptive implant into the fallopian tube may be an intrafallopian contraceptive delivery device such as the one illustrated in FIG. 1a. FIG. 1a illustrates a device similar to the Essure device. The intrafallopian contraceptive delivery device 101 of FIG. 1a is typically formed of a control device, such as a handle 102, a delivery catheter system 103, and a guidewire 104 onto which is held the contraceptive implant to be placed within the fallopian tube. The delivery catheter system 103 contains the guidewire 104, a release catheter (not shown) and the contraceptive implant and the guidewire 104 within the release catheter. The delivery catheter system 103 is transcervically positioned into the uterus and the fallopian tubes via a hysteroscope, such as 100 illustrated in FIG. 1b. The delivery catheter system 103 and guidewire 104 enter the hysteroscope 100 through the working channel 110 of the hysteroscope 100. A distention valve 120 is typically positioned at the tip of the working channel 110. The distention valve 120 seals the entrance of the working channel 110 to prevent a distention fluid, such as saline, to flow out of the hysteroscope 100 as a device such as the delivery catheter system 103 and guidewire 104 of the intrafallopian contraceptive delivery device 101 is introduced into the working channel 110. The opening 130 into the distention valve 120 is designed to prevent the leakage of any fluid out of the hysteroscope 100 and therefore has the smallest opening possible to allow a very tight fit between the device and the valve opening. To prevent damaging the tip 105 of the guidewire 104 or the contraceptive implant to be inserted into the fallopian tube, the guidewire 104 and delivery catheter system 103 are introduced into the distention valve 120 through an introducer sheath 140. The introducer sheath 140 is formed of a soft flexible material such as plastic or Teflon and has a slit 145 to aid in grasping and in the removal of the introducer sheath 140. The introducer sheath 140 must therefore be inserted into the opening 130 of the distention valve 120 while on a stiff mandrel 150 as illustrated in FIG. 1b. Once the mandrel 150 are placed within the distention valve 120 and the channel 110 to the desired depth the mandrel 150 is removed, leaving the introducer sheath 140 within the working channel 110 and the distention valve 120 as illustrated in FIG. 1c. After placing the introducer sheath 140 into the distention valve 120 the tip 105 of the guidewire 104 and the delivery catheter system 103 may be inserted into the introducer sheath 140 and introduced into the distention valve 120 and the working channel 110 as illustrated in FIG. 1d. The introducer sheath 140 may then be removed. The distention valve 120 may have a tight opening that places pressure on the delivery catheter and causes friction. This friction may make the positioning of the insert within the fallopian tubes difficult. Friction may be created even if the introducer sheath 140 is left within the opening 130 of the distention valve 120. The distention valve 120 prevents fluid leakage from the working channel 110. If an introducer sheath 140 is inserted through the distention valve 120, fluid can spray out of the valve and onto the physician or physician's assistant. The amount of fluid spray-back can be significant depending on the fluid pressure used during the procedure.

Once a physician has positioned the delivery catheter system 103 and the guidewire 104 at a position within the fallopian tube where the contraceptive implant may be deposited, it may be awkward and difficult for the physician to maintain the position and may require the physician to use an assistant to aid in the proper stabilization of the system relative to the hysteroscope.

SUMMARY OF THE DESCRIPTION

Various different embodiments are disclosed below and the following summary provides a brief description of only some of these embodiments. According to one aspect of the invention, certain embodiments described below relate to a medical device to stabilize a device for a minimally invasive gynecological procedure with respect to a device that provides a transcervical pathway. The device for the minimally invasive gynecological procedure may be an intrafallopian contraceptive delivery device. The device that provides a transcervical pathway may be a hysteroscope or a catheter. In an embodiment, the stabilization device may maintain a fixed longitudinal distance between an intrafallopian contraceptive device and a hysteroscope. The stabilization device may include a port for the insertion of a catheter to deliver a topical anesthetic or a contrast media to a patient during a minimally invasive gynecological procedure. Further embodiments describe methods of stabilizing the device for the minimally invasive gynecological procedure with respect to the device that provides a transcervical pathway using a stabilization device.

Various other devices and methods for using devices, including kits for use in treating patients, are also described below. Other features of the present invention will be apparent from the accompanying drawings and from the detailed description that follows.

BRIEF DESCRIPTION OF THE DRAWINGS

FIG. 2b is an illustration of a cross-sectional view of the sleeve of the stabilization device of FIG. 2a.

FIG. 5b is an illustration of a cross-sectional view of the distention valve of FIG. 5a.

FIG. 6k illustrates a cut-away side view of a handle of an intrafallopian contraceptive delivery device before tracking forward the delivery catheter.

FIG. 6l illustrates a cut-away side view of a handle of an intrafallopian contraceptive delivery device after tracking forward the delivery catheter.

FIG. 6m illustrates a cut-away view of a handle of an intrafallopian contraceptive delivery device after rolling back a thumbwheel.

FIG. 7a illustrates a cut-away side view of an access catheter.

FIG. 7b illustrates a side view of the outside surface of an access catheter.

FIG. 7c illustrates a side view of an access catheter that has been positioned within the cervix.

FIG. 7d illustrates a side view of the access catheter once the balloon on its distal end has been expanded to fix the position of the access catheter within the cervix.

DETAILED DESCRIPTION OF THE PRESENT INVENTION

Figure 1A:
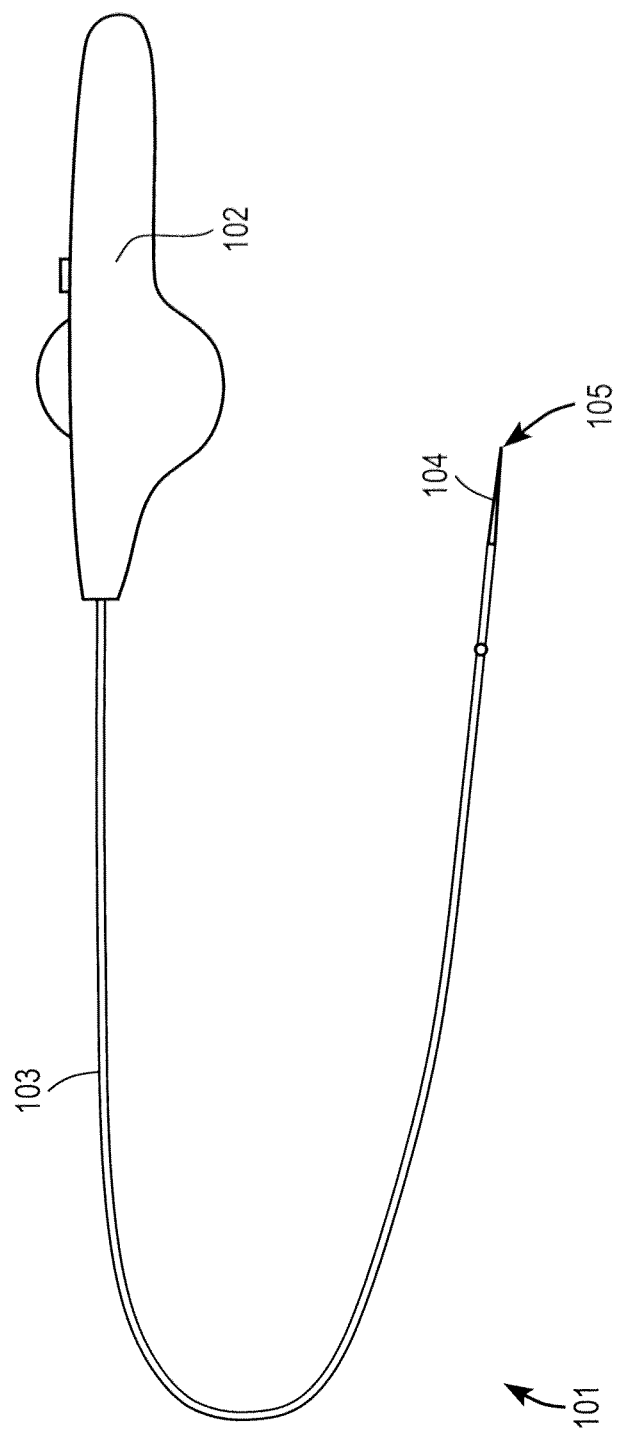
FIG. 1a is an illustration of an intrafallopian contraceptive delivery device.
Figure 1B:
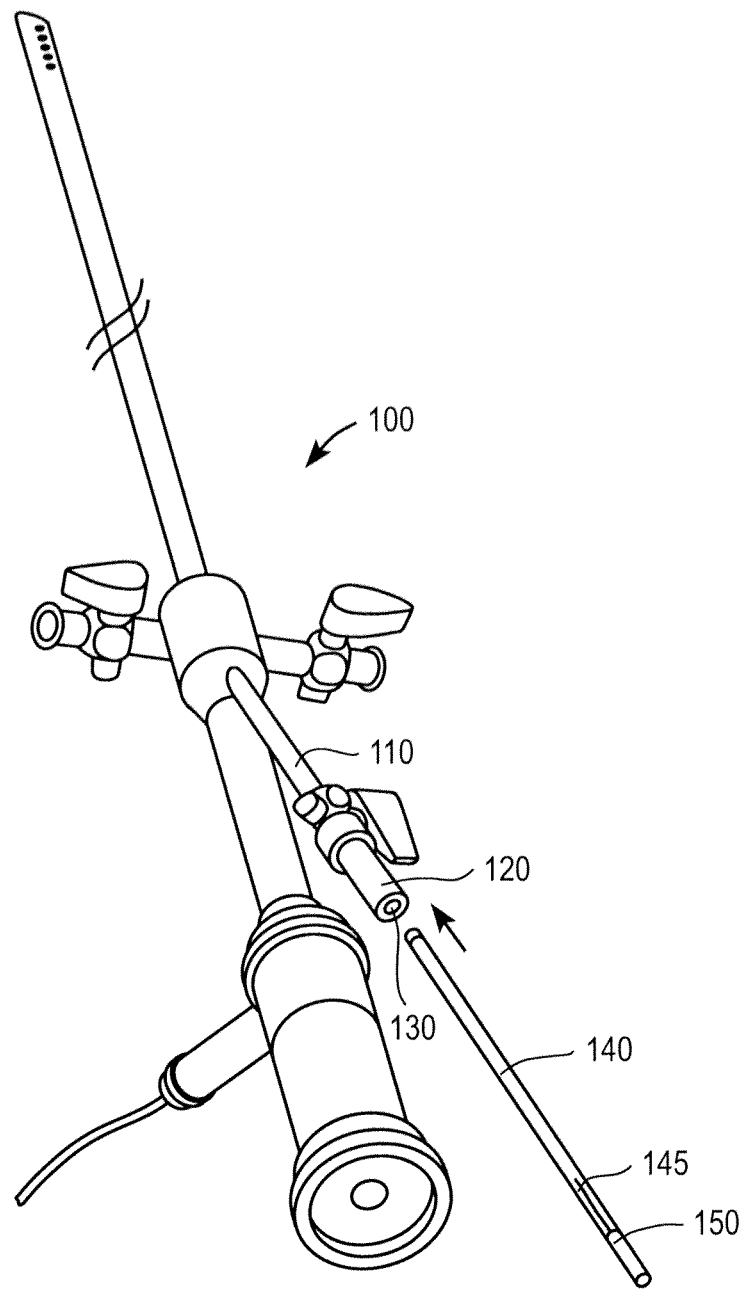
FIG. 1b is an illustration of a hysteroscope and an introducer sheath on a mandrel designed for insertion into a distention valve of a hysteroscope.
Figure 1C:
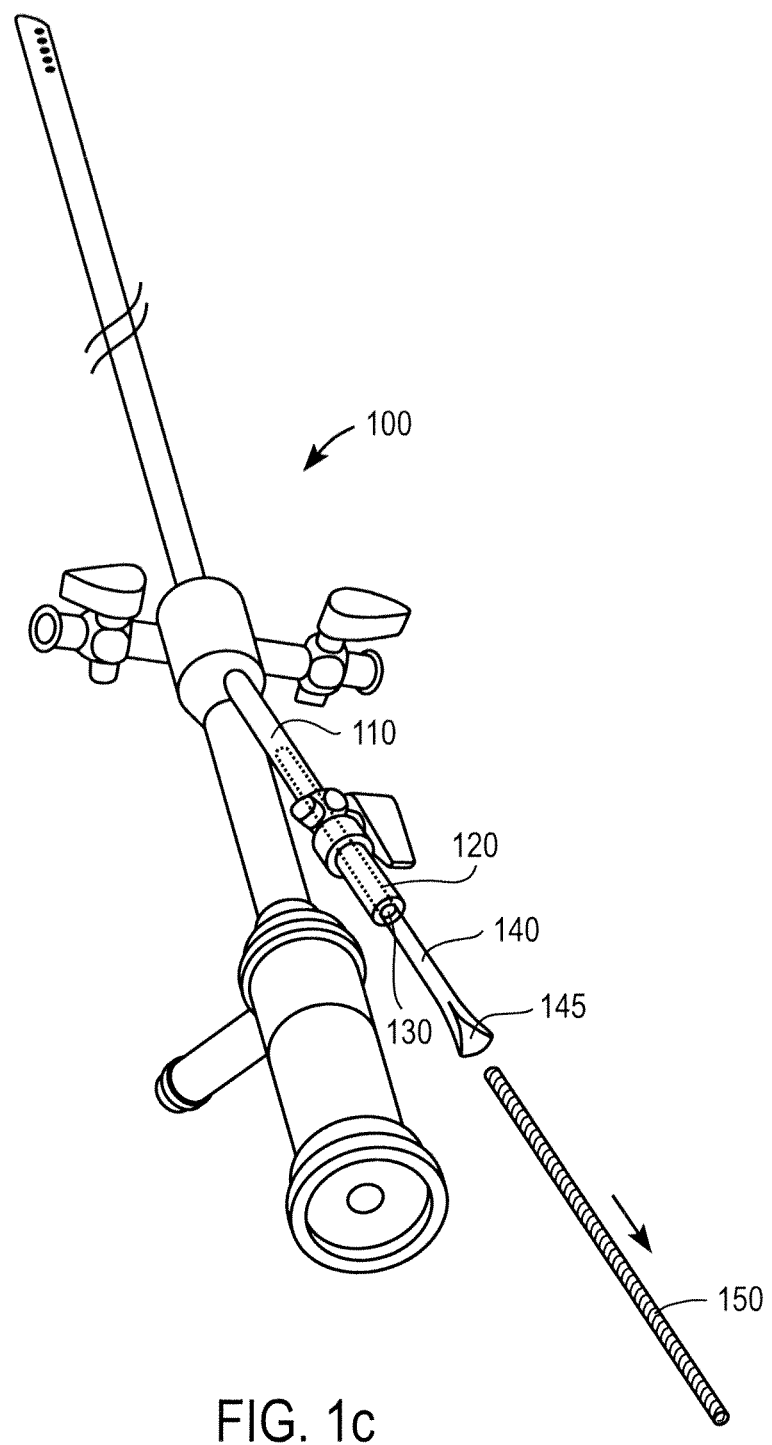
FIG. 1c is an illustration of the hysteroscope of FIG. 1b after the introducer sheath has been inserted into the distention valve of the hysteroscope.
Figure 1D:
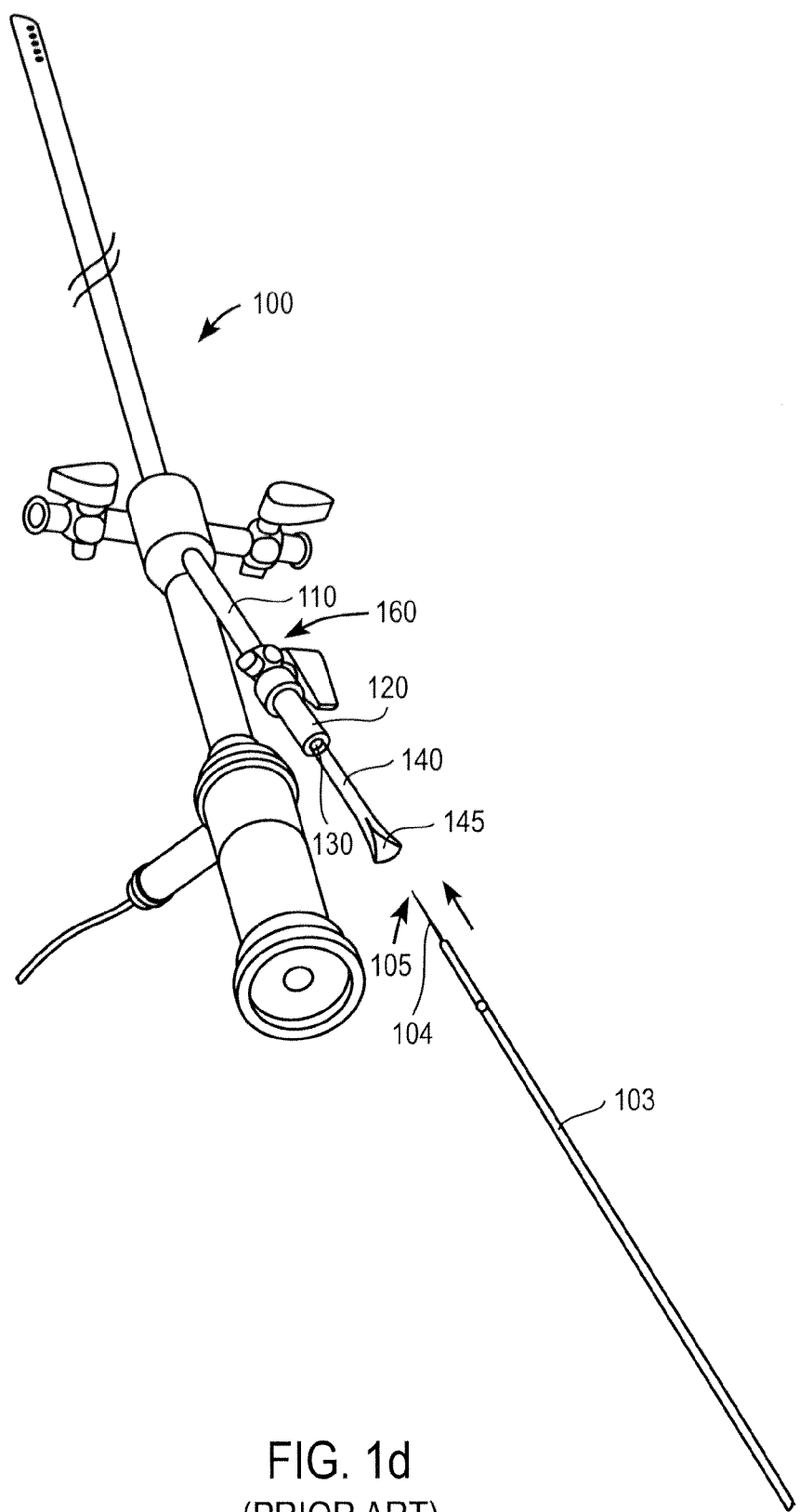
FIG. 1d is an illustration of a delivery catheter of an intrafallopian contraceptive delivery device before its insertion into the introducer sheath and hysteroscope.
Figure 1E:
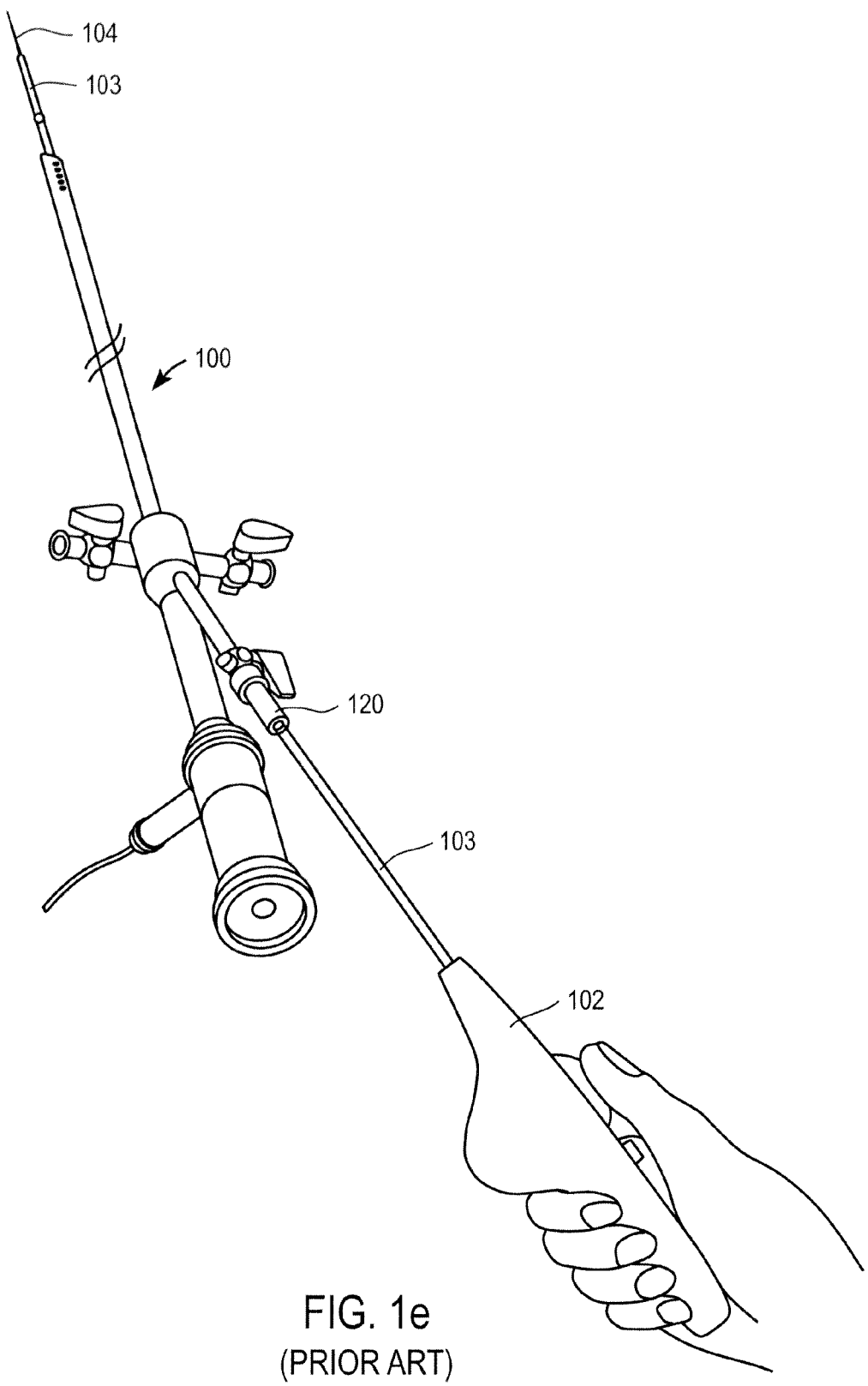
FIG. 1e is an illustration of a delivery catheter of an intrafallopian contraceptive delivery device after its insertion into the hysteroscope and the removal of the introducer sheath.

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well-known or conventional details are not described in order to not unnecessarily obscure the present invention in detail.

The various embodiments of the present inventions provide stabilization devices and methods for use of the stabilization devices with minimally invasive gynecological procedures such as methods of preventing pregnancy by inserting intrafallopian contraceptive devices into the fallopian tubes, the removal of uterine polyps, endometrial ablation, cryotherapy of the uterus, myomectomy, radiologic fibroid embolization, uterine and vaginal relaxation, female urological disorders, dilation and curettage, endometrial biopsy, colposcopy, hysterosalpinograpy, excision of submucous myoma, polypectomy or intrauterine adhesions, laparoscopy, mini-laparoscopy, surgery for urinary incontinence, reconstructive pelvic procedure, treatment for infertility such as renastamosis, selective salpingectomy, salpingostomy, fibrioplasty, and tubal cannulation. The intrafallopian contraceptive devices may provide permanent contraception or sterilization. Examples of contraceptive devices and method for using these devices with delivery systems are provided in U.S. Pat. No. 6,526,979 and U.S. Pat. No. 6,634,361, both of which are incorporated herein by reference. It is to be understood that embodiments of the current invention may also be used with non-gynecological minimally invasive surgeries that employ endoscopes. Examples of non-gynecological minimally invasive surgeries include angioscopy, arthroscopy, bronchoscopy, cystoscopy, solonoscopy, systourethroscopy, esophagogastroduodenoscopy, gastroscopy, largyngoscopy, protosigmoidoscopy, rhinolaryngoscopy, subfacial edoscopic perforating vein surgery, and sigmoidoscopy.

The delivery systems for the intrafallopian contraceptive devices are generally formed of a catheter containing the contraceptive device or devices and a handle that is used to control the placement of the catheter. The intrafallopian contraceptive devices may be positioned by the retraction of the catheter to expose the contraceptive device and the deposition of the contraceptive device within the fallopian tube. The stabilization devices are adapted to be coupled to a control device of an intrafallopian contraceptive delivery device, such as the handle of the delivery systems described in the above-referenced patents, and to a device that provides a pathway through the cervix to maintain a fixed longitudinal distance between the control device and the device that provides a pathway through the cervix. This device may free up one of the hands of a physician performing the procedure by maintaining the fixed distance between the control device and an endoscope. Examples of endoscopes include a hysteroscope, an angioscope, an arthroscope, a bronchoscope, a choledochoscope, a colonoscope, a colposcope, a cystoscope, a cystourethroscope, a duodenoscope, an esophagoscope, an esophagogastroduodenoscope, a falloposcope, a gastroscope, a laryngoscope, a laparoscope, a mini-laparoscope, an ostoscope, an opthalmoscope, a proctoscope, a proctosigmoidoscope, a sigmoidoscope, and a thoracoscope.

In an embodiment, the endoscope may be a hysteroscope for gynecological procedures such as the placement of the contraceptive devices within the fallopian tubes. The accuracy of the placement of the contraceptive devices within the fallopian tubes may be increased due to the greater stabilization and the standardization of the longitudinal distance between the control device and the hysteroscope. In an embodiment, the stabilization device may also facilitate the delivery of a topical anesthetic to the cervix and the uterus. In another embodiment, the stabilization device may facilitate the delivery of a contrast media into the uterus for ultrasound or radiography.

The stabilization device is formed of a means for coupling the stabilization device to a device for a minimally invasive gynecological procedure and of a means for coupling the stabilization device to a device that provides a transcervical pathway. The device that provides a transcervical pathway may be a hysteroscope or a catheter, for example. By coupling the stabilization device to both the device for the minimally invasive gynecological procedure and the device that provides a transcervical pathway, the stabilization device may stabilize the position of the device for the minimally invasive gynecological procedure with respect to the device that provides a transcervical pathway. The stabilization of these devices with respect to one another may facilitate the ease with which the gynecological procedures are performed as well as increase the accuracy of the gynecological procedures. For example, the stabilization device may be adapted to be coupled to an intrafallopian contraceptive delivery device and to a hysteroscope to maintain a fixed longitudinal distance between the intrafallopian contraceptive device and the hysteroscope.

Figure 2A:
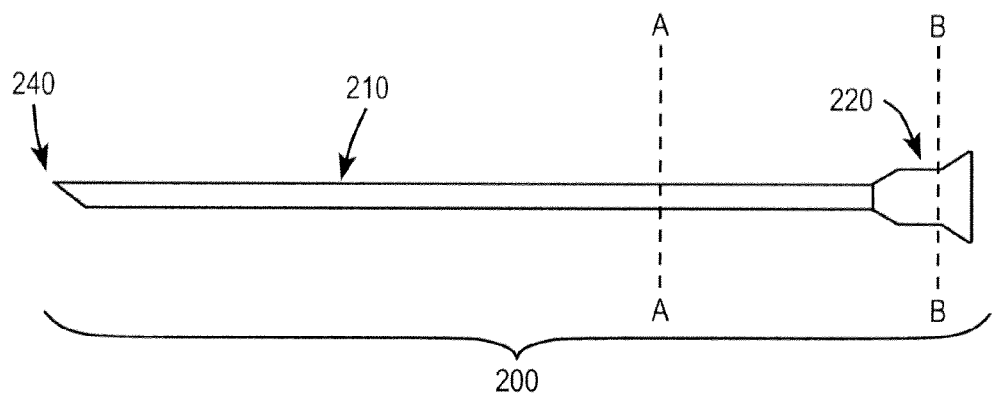
FIG. 2a is an illustration of a side view of a stabilization device formed of a sleeve and a mechanical means for coupling the proximal end of the stabilization device to a control device of a device for a gynecological procedure.

In one embodiment, the stabilization device may be a sleeve such as the one illustrated in FIG. 2a. FIG. 2a illustrates a stabilization device 200 formed of a sleeve 210 and a means 220 for coupling the stabilization device to a control device of an intrafallopian contraceptive device. The sleeve 210 may be formed of a material having a stiffness sufficient to stabilize the control device with respect to the hysteroscope. Any hysteroscope that is capable of performing the methods described herein may be used, but in particular embodiments the hysteroscope may be an Olympus Storz Bettocchi, a Wolf, a Wolf 45° "Panoview Plus", or a Circon ACMI. The material used to form the sleeve 210 may be a metal such as stainless steel or nitinol or a material such as polycarbonate or PEEK (polyetheretherketone). The sleeve 210 may also be coated with a soft polymer coating to increase the ability of the ball valve within the channel of the hysteroscope to grip the stabilization device 200 and to hold it in place. The sleeve may have a length in the approximate range of 1 cm and 150 cm, and more particularly in the range of 3.5 cm and 12.0 cm. The length of the sleeve may vary depending on the use. In an embodiment, the sleeve may have a length sufficient to extend through a working channel of a hysteroscope. In another embodiment the sleeve may have a length sufficient to extend through the entire length of a hysteroscope. In an alternate embodiment, the sleeve may have a length sufficient to reach the fallopian tubes through a device that provides a transcervical pathway, such as a catheter.

Figure 2B:
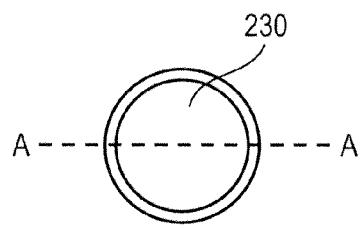
Figure 2C:
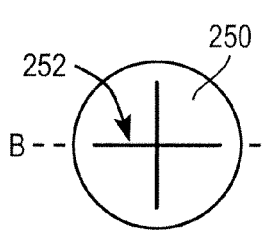
FIG. 2c is an illustration of a cross-sectional view of a transverse membrane within the stabilization device of FIG. 2a having a cross-hatched opening.
Figure 2D:
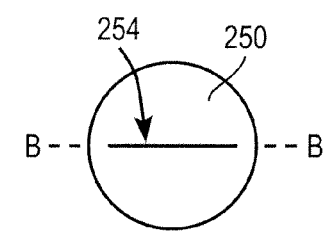
FIG. 2d is an illustration of a cross-sectional view of a transverse membrane within the stabilization device of FIG. 2a having a slit opening.
Figure 2E:
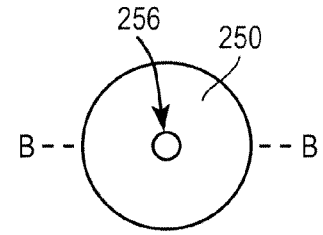
FIG. 2e is an illustration of a cross-sectional view of a transverse membrane within the stabilization device of FIG. 2a having a hole opening.

The sleeve 210 has a lumen 230 extending longitudinally through the entire sleeve. The lumen 230, as illustrated in a cross-section A-A in FIG. 2b, has a diameter large enough to fit around a catheter that is part of a delivery device for an intrafallopian contraceptive device. This is to prevent friction between the sleeve 210 and the delivery catheter during insertion of the delivery catheter and guide wire and during retraction of the delivery catheter. In an embodiment, the diameter of the lumen 230 may be in the approximate range of 2 French and 9 French, and in another embodiment may have a diameter of approximately 5 French. The distal end 240 of the stabilization device 200 may be tapered as illustrated in FIG. 2a to enable the distal end to be fitted into a distention valve of a hysteroscope. The selection of the shape of the distal end 240 of the stabilization device 200 may be influenced by the shape of the opening into the rubber-like material of the distention valve as well as the stiffness of the rubber-like material that forms the distention valve. A tapered distal end 240 of the stabilization device 200 may be valuable for insertion of the stabilization device 200 into a stiff or tight opening in the distention valve. In an alternate embodiment the distal end 240 of the stabilization device 200 may be blunt, such as in embodiments where the distention valve is part of the stabilization device 200. The means for coupling the stabilization device to the device that provides a transcervical pathway, such as the control device of an intrafallopian contraceptive device, may be a mechanical fitting such as that illustrated in FIG. 2a at the proximal end of the sleeve 210. The mechanical fitting 220 may include a transverse membrane 250 to prevent the backflow of fluid from the hysteroscope from spilling out onto the operator and the control device of the intrafallopian contraceptive delivery device. The transverse membrane 250 is illustrated in FIGS. 2c, 2d, and 2e as the B-B cross-section of the mechanical fitting 220. The transverse membrane 250 is formed with an opening through which the catheter of the intrafallopian contraceptive delivery device can fit. The opening in the transverse membrane forms a seal around the catheter to prevent the backflow of fluid. The opening may be a crosshatch seal 252 as illustrated in FIG. 2c, a slit seal as illustrated in FIG. 2d, or a hole seal as illustrated in FIG. 2e. In alternate embodiments the transverse membrane 250 may be a double membrane having different or the same combinations of the various types of seals. For example, the double membrane may be a combination of a slit seal and a hole seal, a hole seal and a slit seal, a hole seal and a crosshatch seal. The seal combinations of the double membrane may also vary with respect to which seal is distal and which seal is proximal.

Figure 2F:
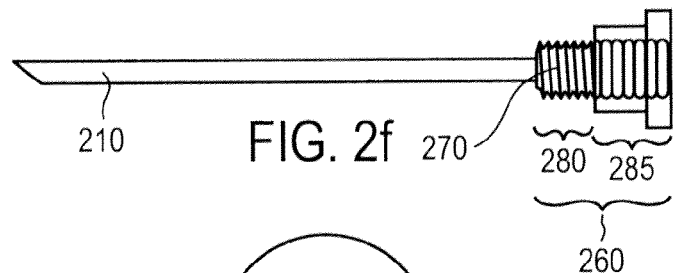
FIG. 2f is an illustration of a side view of a stabilization device formed of a sleeve and an adjustable O-ring for coupling the proximal end of the stabilization device to a device for a gynecological procedure.
Figure 2G:
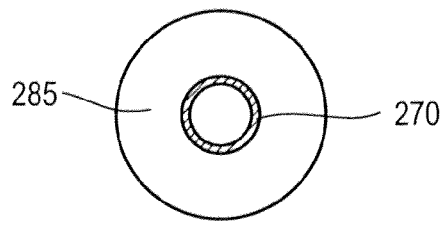
FIG. 2g is an end-on view of the proximal end of the adjustable O-ring in an open position.
Figure 2H:
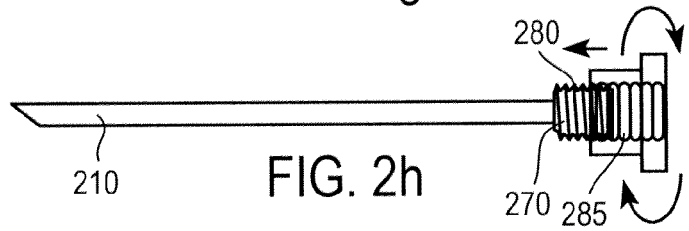
FIG. 2h is a side view of the stabilization device of 2f after screwing down the adjustable O-ring to partially close the O-ring.
Figure 2I:
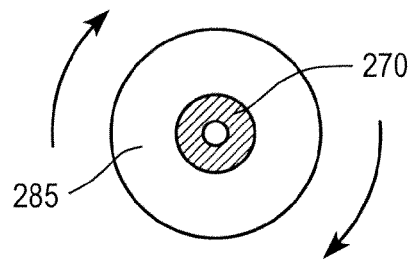
FIG. 2i is an end-on view of the proximal end of the partially closed adjustable O-ring of FIG. 2h.
Figure 2J:
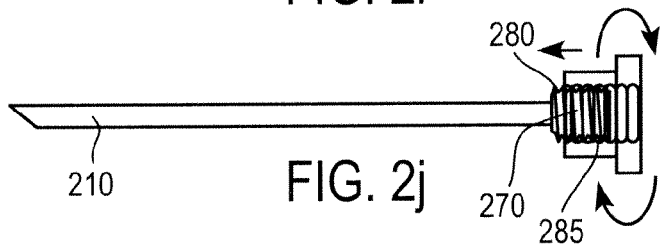
FIG. 2j is a side view of the stabilization device of FIG. 2h after further screwing down the adjustable O-ring to close the O-ring.
Figure 2K:
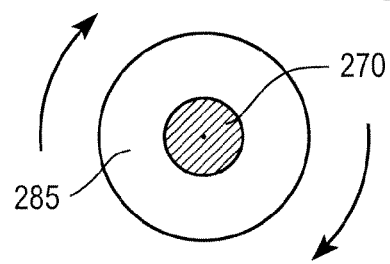
FIG. 2k is an end-on view of the distal end of the closed adjustable O-ring of FIG. 2j.

In an alternate embodiment, the means for coupling the stabilization device 200 to the delivery catheter of a device for a minimally invasive gynecological procedure, such as an intrafallopian contraceptive delivery device, may be an adjustable O-ring 260 such as that illustrated in FIGS. 2f-2k. FIGS. 2f and 2g illustrate the adjustable O-ring 260 in a fully open position. The adjustable O-ring is formed of an O-ring within a first sleeve 280. The outer surface of the first sleeve 280 has screw threads that are threaded by the screw threads inside the second sleeve 285. In the fully open position, the second sleeve 285 has not been screwed onto the first sleeve 280. FIGS. 2h and 2i illustrate the adjustable O-ring after the second sleeve 285 has been screwed onto the first sleeve 280 to reduce the diameter of the O-ring 270. Continuing to screw the second sleeve 285 onto the first sleeve 280 will seal closed the O-ring 270 completely, as illustrated in FIGS. 2j and 2k. The adjustable O-ring may be adjusted to form a seal around a delivery catheter to hold the stabilization device 200 in place. The seal also serves to prevent backflow of fluid from the hysteroscope out of the stabilization device 200.

Figure 2L:
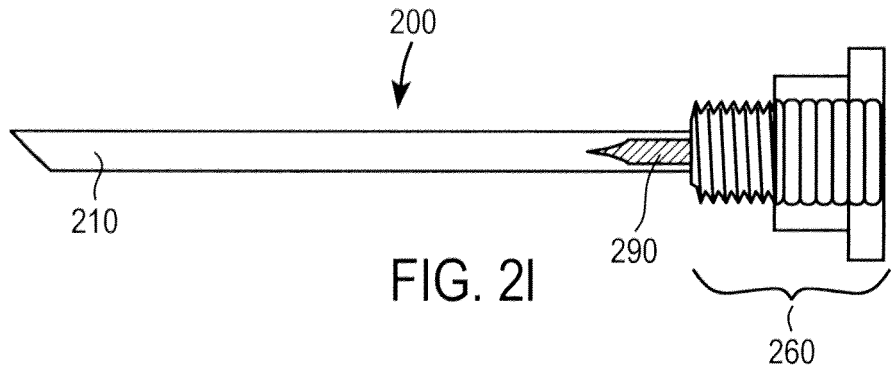
FIG. 2l is an illustration of a side view of a stabilization device formed of a sleeve, an adjustable O-ring, and a duckbill valve.
Figure 2M:
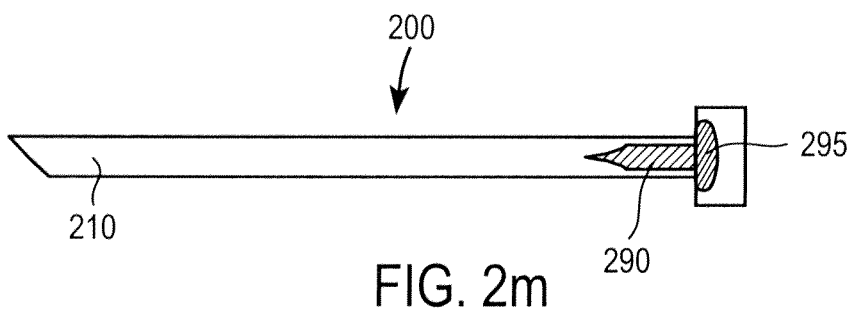
FIG. 2m is an illustration of a side view of a stabilization device formed of a sleeve, an O-ring, and a duckbill valve.
Figure 2N:
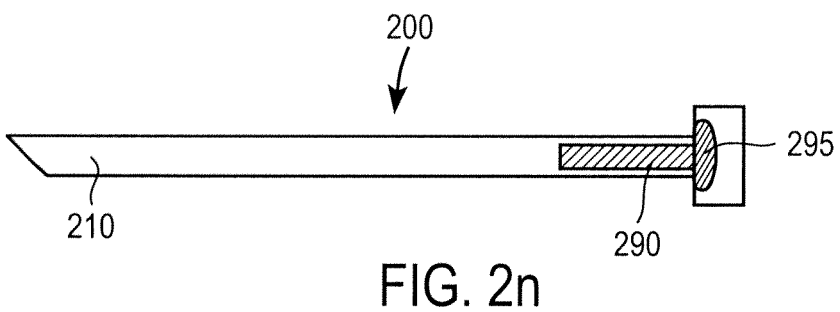
FIG. 2n is an illustration of a top view of the duckbill valve of FIG. 2m.
Figure 2O:
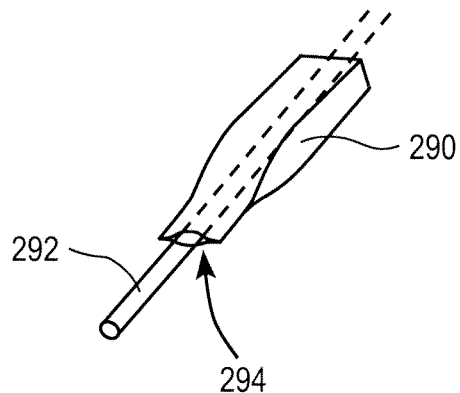
FIG. 2o is an illustration of a detailed view of the duckbill valve of FIGS. 2l-2n through which a catheter has been inserted.

As illustrated in FIG. 2l, the stabilization device may further include a duckbill valve 290. The duckbill valve 290 may be coupled to the adjustable O-ring 260 at the proximal end of the sleeve 210 to form a continuous lumen with the adjustable O-ring 260. The duckbill valve 290 may provide a further seal to prevent the backflow of fluid out of stabilization device 200, particularly when tightening the adjustable O-ring 260 onto a delivery catheter. The duckbill valve 290 may also be used in combination with a non-adjustable O-ring 295. FIG. 2m illustrates a side-view of the duckbill valve 290 in combination with the non-adjustable O-ring 295. FIG. 2n illustrates a top-view of the duckbill valve 290 in combination with the non-adjustable O-ring 295. The non-adjustable O-ring 295 may have an opening having a diameter sufficient to form a seal around a delivery catheter. In this embodiment, the duckbill valve 290 also serves to further prevent the backflow of fluid out of the stabilization device 200. The non-adjustable O-ring 295 may also be used alone, without the duckbill valve 290, as a means for coupling the stabilization device 200 to a device for a gynecological procedure. A detailed view of the duckbill valve 290 is illustrated in FIG. 2o. FIG. 2o illustrates a catheter 292 through a lumen in the center of the duckbill valve 290. The catheter 292 exits the duckbill valve 290 through a slit seal 294 at the distal end (the duckbill) of the duckbill valve 290. Because the duckbill valve 290 is formed of a flexible rubber-like material the slit seal 294 of the duck bill valve 290 forms a seal around the catheter 292.

Figure 3A:
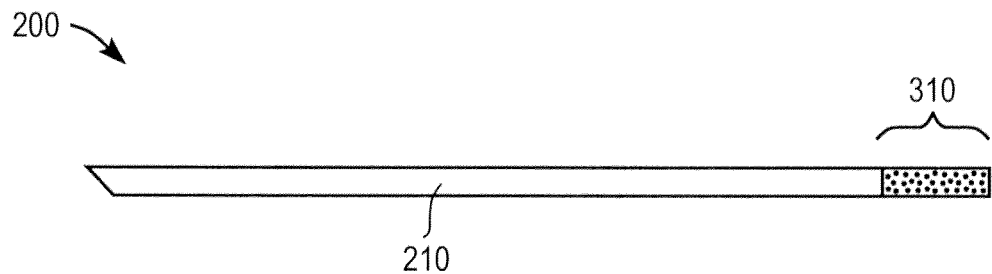
FIG. 3a is an illustration of a side view of a stabilization device formed of a sleeve and of a textured friction fitting.
Figure 3B:
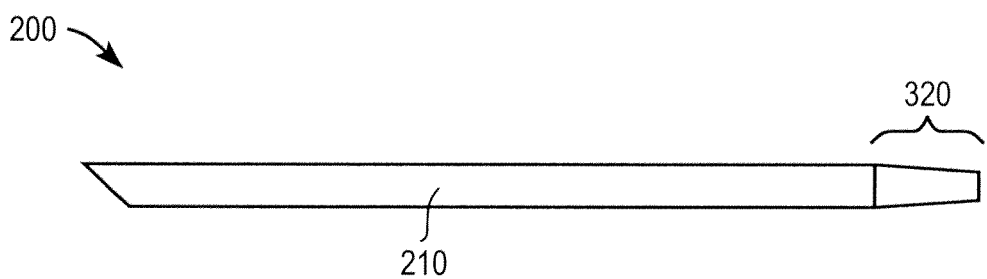
FIG. 3b is an illustration of a side view of a stabilization device formed of a sleeve and of a tapered friction fitting.
Figure 3C:
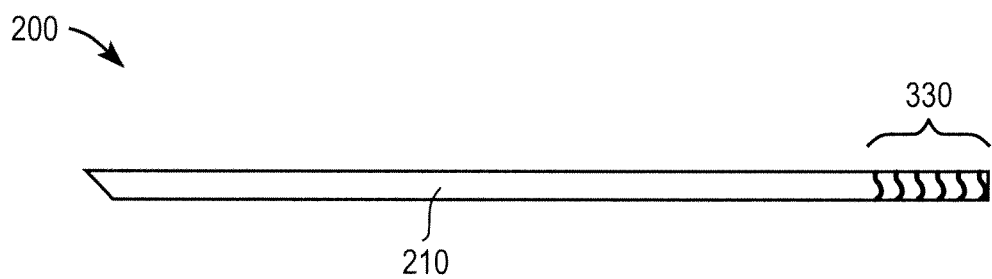
FIG. 3c is an illustration of a side view of a stabilization device formed of a sleeve and of a screw fitting.

The means for coupling the stabilization device 200 to the control device of the intrafallopian contraceptive delivery device may alternatively be a friction fitting that is designed to fit into a control device of a device for a gynecological procedure, such as the handle of an intrafallopian contraceptive delivery device. The friction fitting may be formed as a textured portion 310 on the distal end of the sleeve 210 as illustrated in FIG. 3a, as a portion of the sleeve 210 with a more narrow diameter 320 as illustrated in FIG. 3b, or a portion of the sleeve 210 having a screw thread 330 as illustrated in FIG. 3c.

Figure 4A:
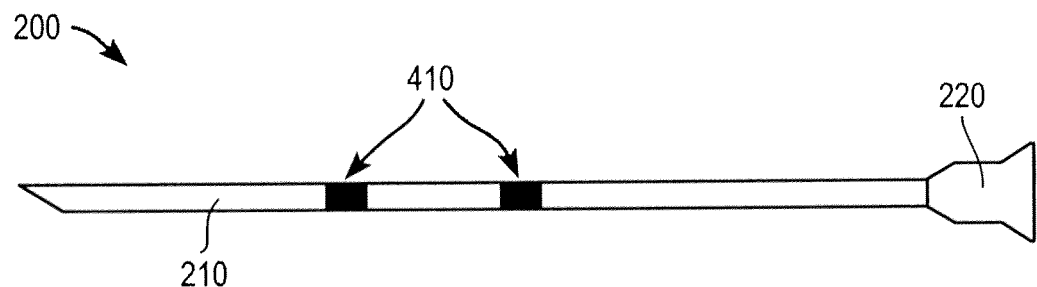
FIG. 4a is an illustration of a side view of a stabilization device having a first marker and a second marker on the outside of the sleeve.
Figure 6A:
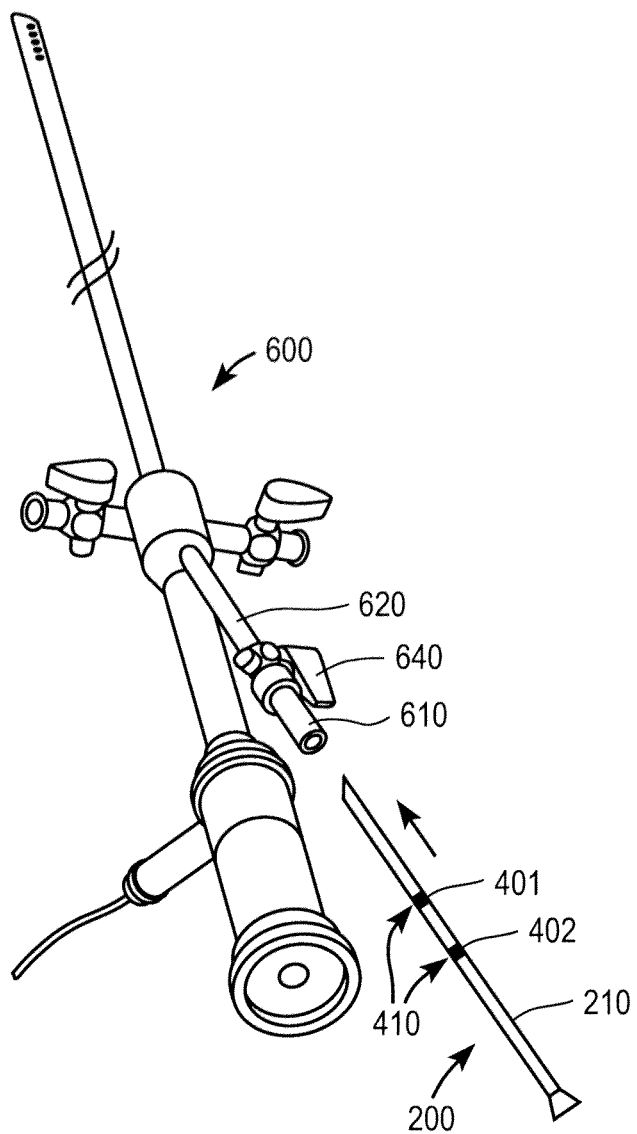
FIG. 6a illustrates a hysteroscope and a stabilization device positioned for insertion into the distention valve of the hysteroscope.
Figure 6B:
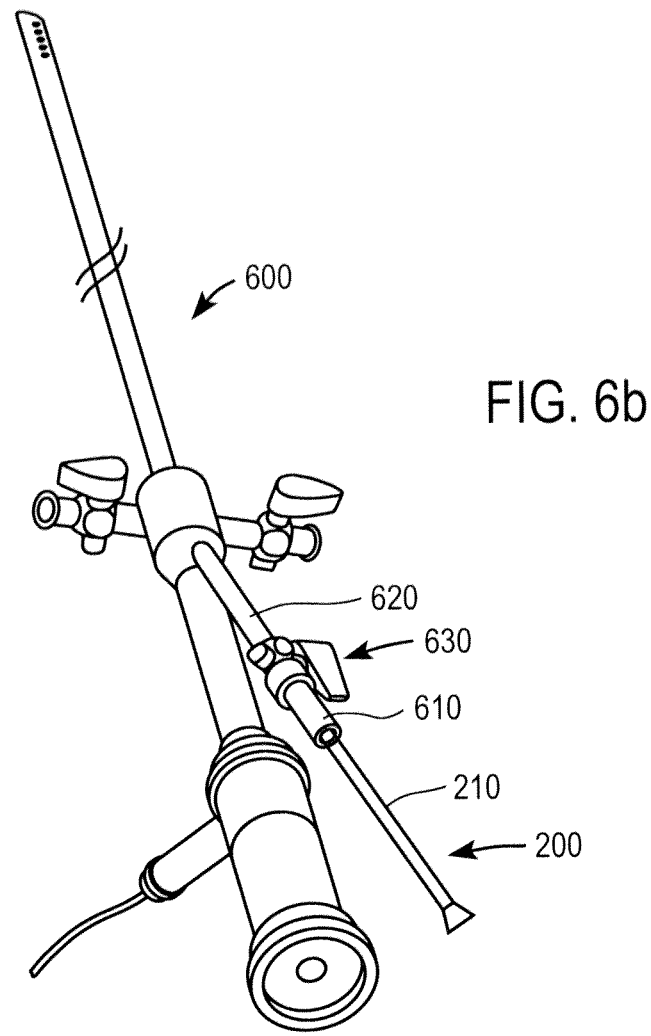
FIG. 6b illustrates a stabilization device inserted into a distention valve and a channel of the hysteroscope.
Figure 6C:
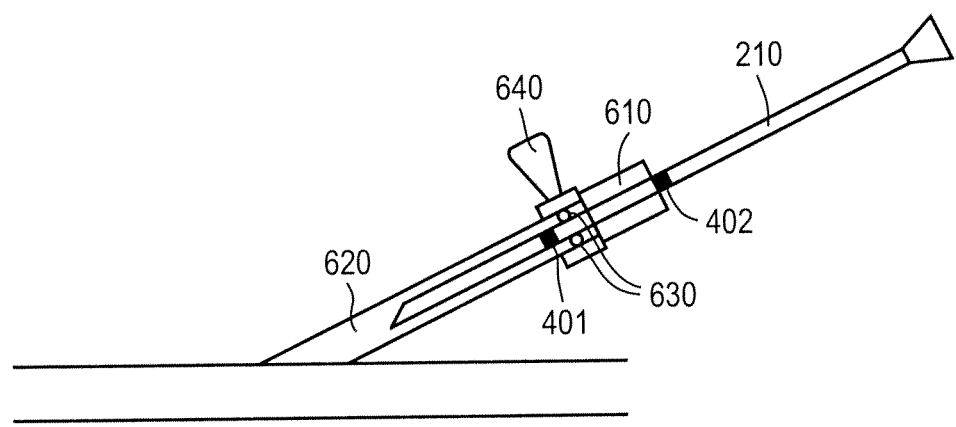
FIG. 6c illustrates a cut-away side view of the stabilization device within the distention valve and channel of the hysteroscope.

In another embodiment, the stabilization device of FIG. 2a may have an insertion marker 410 as illustrated in FIG. 4a on an outside surface of the sleeve 210 at a position selected to indicate that the distal end of the sleeve has been inserted to a predetermined distance into the distention valve and working channel of the hysteroscope. FIG. 4a illustrates an insertion marker 410 formed of two markings, a distal marking 401 and a proximal marking 402, on the outside of the sleeve 210. In an embodiment illustrated in FIG. 6a, the stabilization device 200 is inserted into the distention valve 610 of a hysteroscope 600 such that the distal marking 401 is inserted completely within the distention valve 610 and the working channel 620 of the hysteroscope 600 and the proximal marking 402 is outside of the distention valve 610 as illustrated in FIGS. 6b and 6c. In an embodiment, the proximal marking 402 is positioned so that the distal end of the stabilization device is inserted into the working channel to a depth sufficient to be clamped by the ball valve clamps 630 of the port valve switch 640. By inserting the stabilization device past the ball valve clamps 630 the possibility that the ball valve clamps may pinch or cut the delivery catheter of the intrafallopian contraceptive delivery device may be minimized. FIG. 6c illustrates a cut-away view of the inside of the distention valve 610 and the working channel 620 of the hysteroscope 600. Other embodiments of the insertion marker 410 are also contemplated by the invention, such as a single marking on the outside surface of the sleeve 210.

Figure 4B:
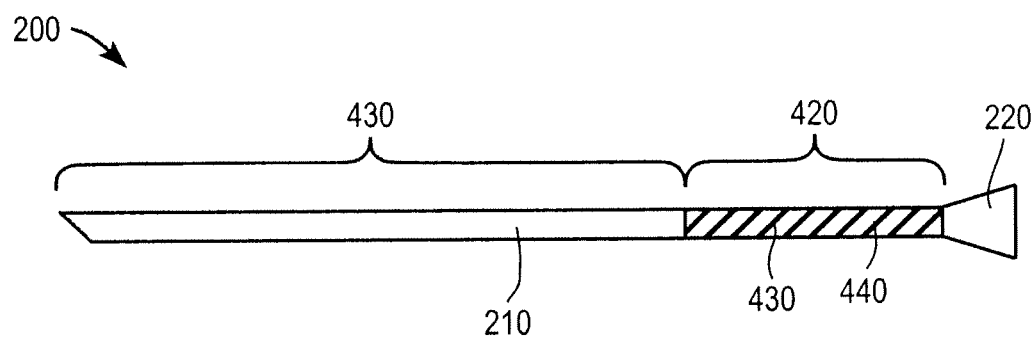
FIG. 4b is an illustration of a side view of a stabilization device formed of a sleeve having a flexible portion and an inflexible portion.
Figure 4C:
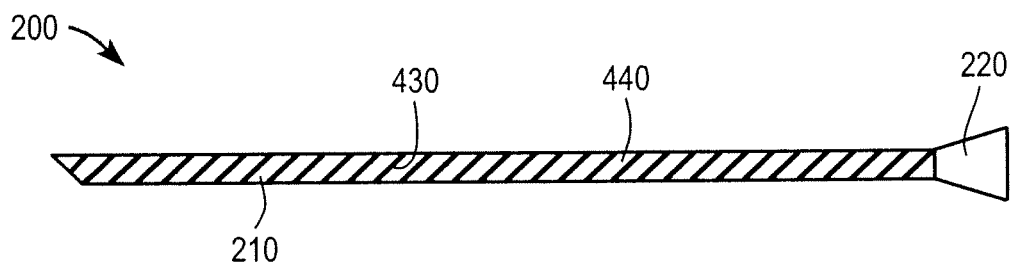
FIG. 4c is an illustration of a side view of a stabilization device formed of a flexible sleeve.
Figure 4D:
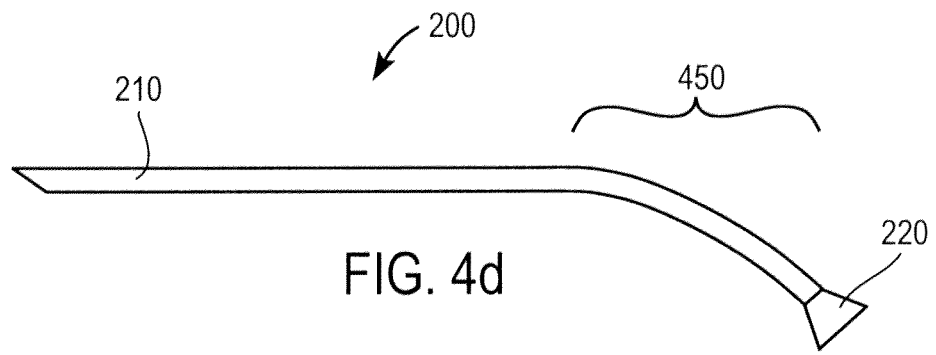
FIG. 4d is an illustration of a side view of a stabilization device formed of a sleeve curved on the proximal end.

FIG. 4b illustrates yet another embodiment of the stabilization device 200 where a portion 420 of the sleeve 210 is flexible and a portion 430 is inflexible. In some instances it may be beneficial for the stabilization device to have some flexibility to increase the maneuverability of the intrafallopian contraceptive delivery device to aid in the positioning of the insert within the fallopian tube. The flexibility of the sleeve 210 may also be valuable in enabling the operator of the delivery device to maneuver the handle around the hysteroscope if the angle of the working channel on the hysteroscope is close to the body of the hysteroscope. The flexible portion 420 of the sleeve 210 may be formed of a coil 430 coated with a polymer tubing material 440 that may also coat the inflexible portion 430. In an alternate embodiment, the entire sleeve 210 may be flexible. In one embodiment the flexible sleeve 210 illustrated in FIG. 4c may be formed of a coil 430 coated with a polymer tubing material 440.

Figure 4E:
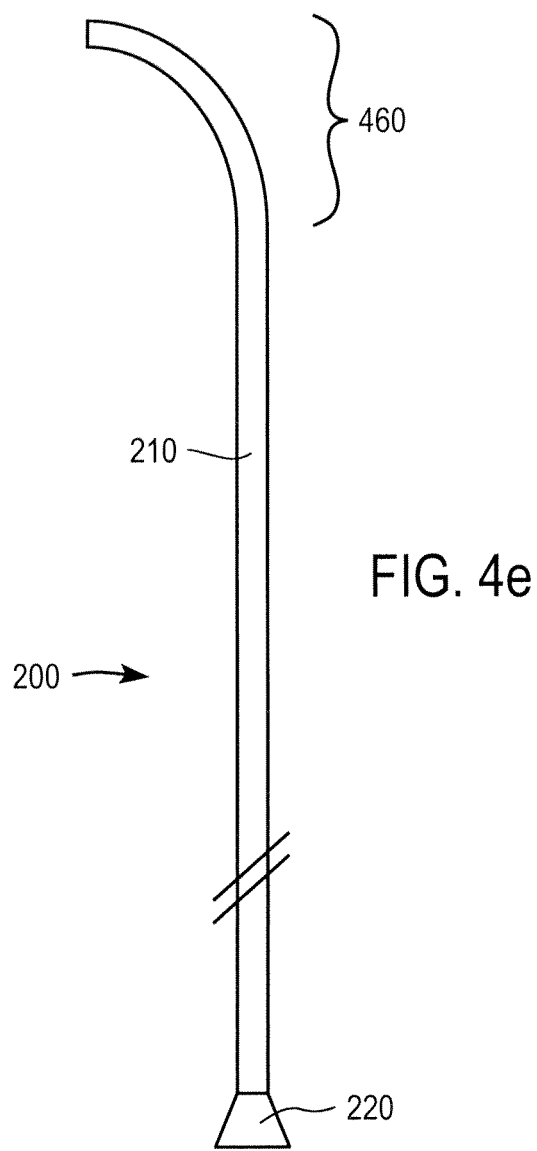
FIG. 4e is an illustration of a side view of a stabilization device formed of a sleeve curved on the distal end.

In another embodiment the sleeve 210 of the stabilization sheath 200 may have a curved portion to increase the maneuverability of the device for the gynecological procedure. The sleeve 210 may have a proximal curved portion 450 as illustrated in FIG. 5d. Alternatively the sleeve 210 may have a distal curved portion 460 as illustrated in FIG. 4e. The distal curved portion 460 may facilitate the positioning of a fallopian tube insert from an intrafallopian contraceptive delivery device into a fallopian tube. In this embodiment the sleeve 210 may have a length sufficient to reach the fallopian tubes. The distal curved portion 460 may be formed of an inflexible material or it may be formed of a flexible material that may be bent at a desired angle by using adjustment wires (not illustrated) that would run the length of the sleeve 210 up to the distal curved portion.

Figure 4F:
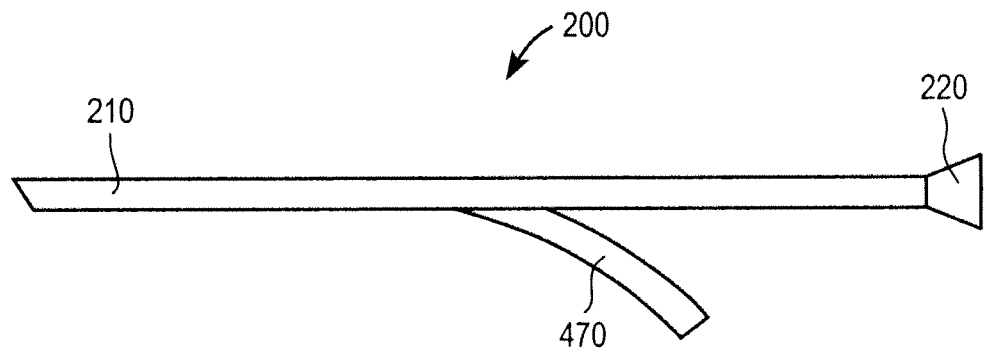
FIGS. 4f and 4g illustrate two embodiments of a stabilization devices which include at least one additional port.
Figure 4G:
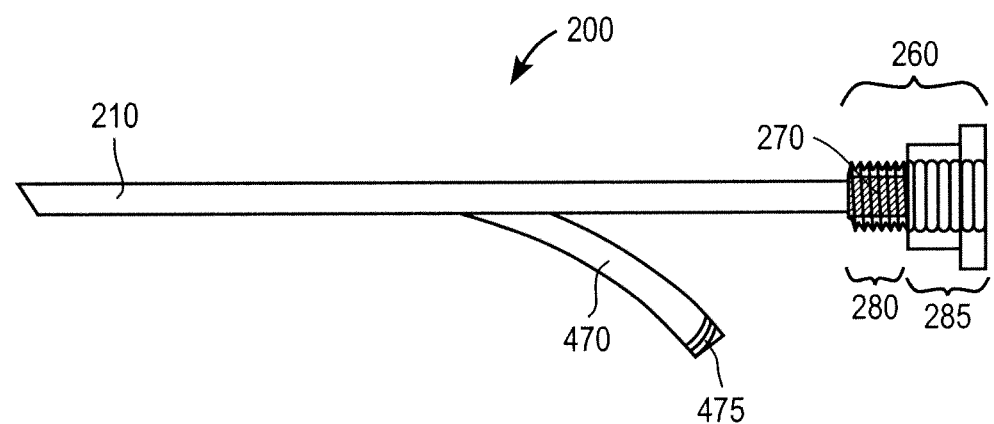

FIGS. 4f and 4g illustrate two embodiments of a stabilization device 200 having an additional port 470. The port 470 has a lumen continuous with the lumen of the sleeve 210. An additional delivery catheter may be inserted into a device that provides a transcervical pathway through the port 470, in addition to a delivery catheter that is coupled to a device for a gynecological procedure. In an embodiment, the port 470 may provide a pathway for an anesthetic delivery catheter or a contrast media delivery catheter. The port 470 may be straight or slightly curved and jutting from the sleeve 210 at any angle that is practical for the insertion of a catheter. In an embodiment illustrated in FIG. 4g the port 470 may have a screw thread 475 on the proximal end for the attachment of a screw-on device such as the tip of a syringe.

Figure 5A:
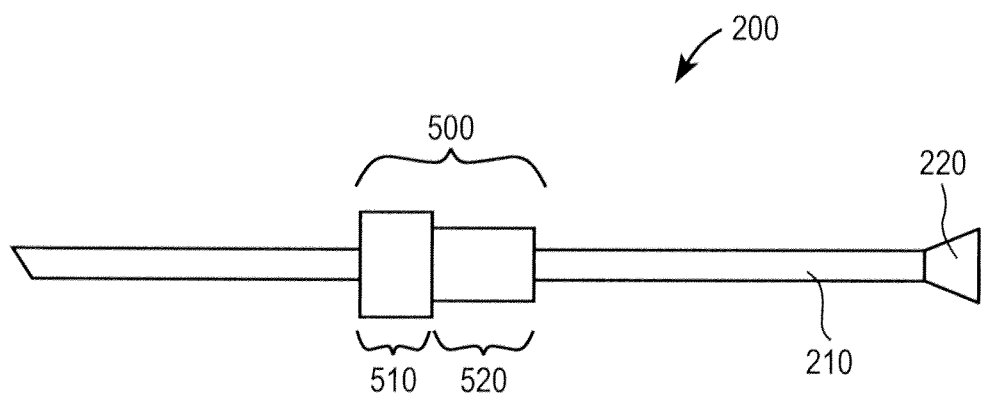
FIG. 5a is an illustration of a side view of a stabilization device having an embodiment of a distention valve for a hysteroscope attached to the sleeve.
Figure 5B:
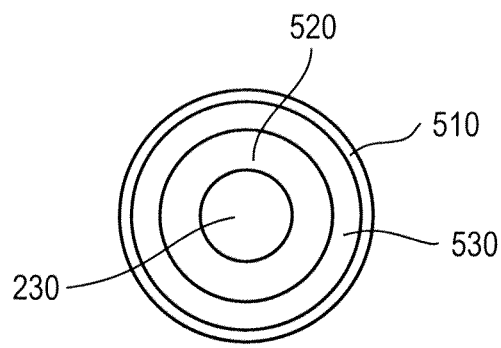
Figure 5C:
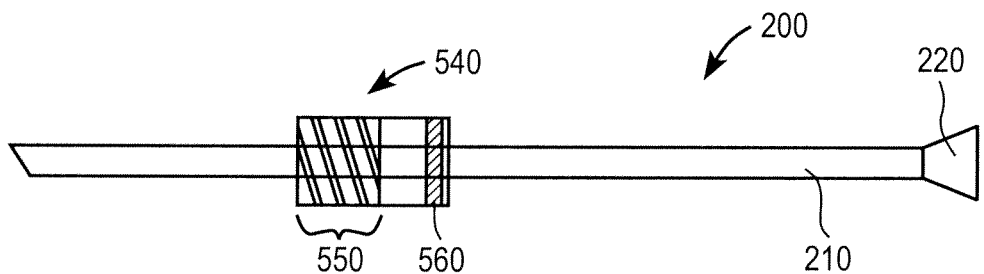
FIG. 5c is an illustration of a cross-sectional view of a stabilization device having another embodiment of a distention valve for a hysteroscope attached to the sleeve.
Figure 5D:
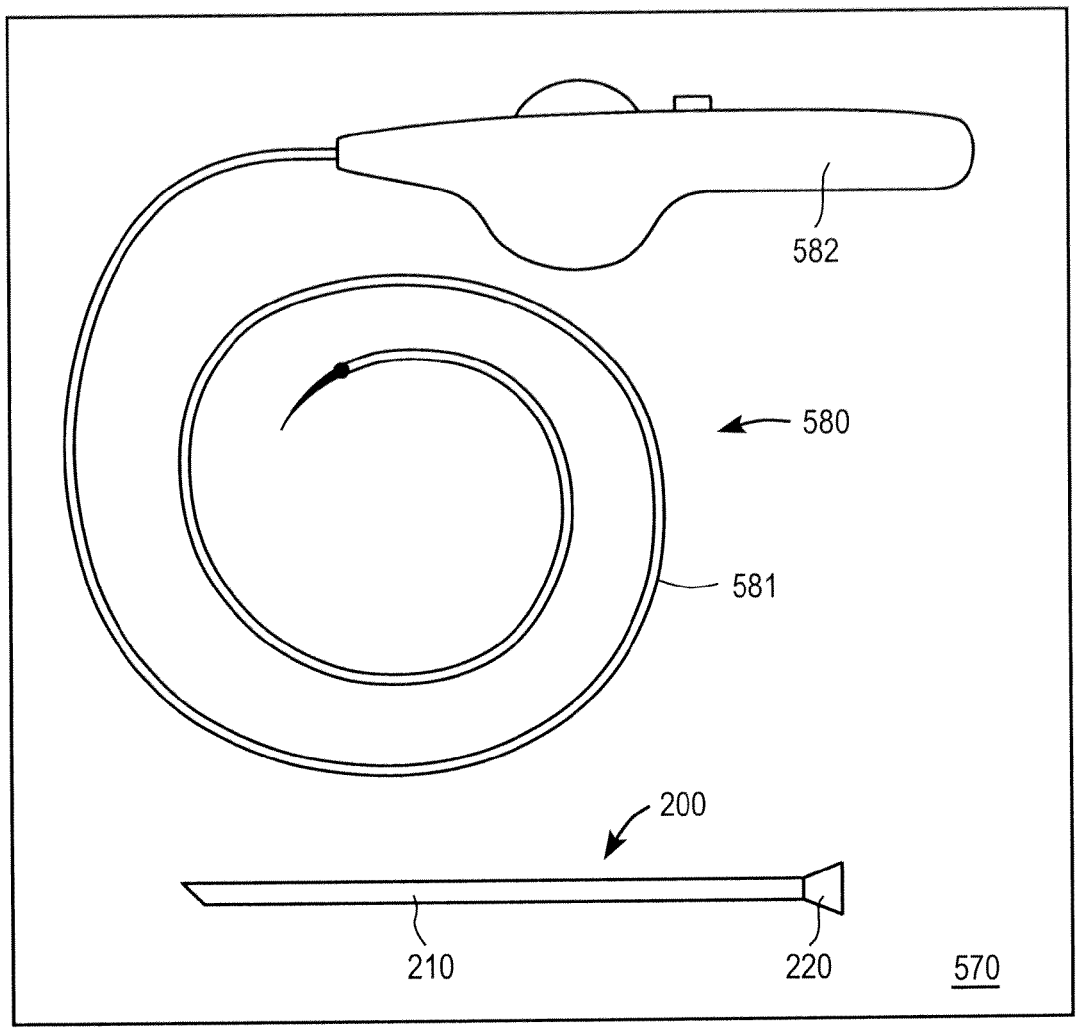
FIG. 5d illustrates a kit containing a stabilization device and an intrafallopian contraceptive delivery device.

FIG. 5a illustrates a stabilization device 200 that has a distention valve 500 coupled to the distal end of the sleeve 210. The distention valve may be formed of a soft rubber-like material that can form a seal around the working channel of a hysteroscope or another type of device that provides a transcervical pathway to prevent the backflow of fluid. In this exemplary embodiment the distention valve 500 is formed of a portion 510 that fits around a working channel of a hysteroscope. As illustrated in FIGS. 5a and 5b, the portion 520 of the distention valve 500 may have a smaller diameter than the portion 510 such that a shelf 530 is formed. The distention valve 500 couples to the sleeve 210 of the stabilization device 200 to form a continuous lumen between the distention valve 500 and the sleeve 210. In alternate embodiments the distention valve 500 may have a single diameter without the shelf 530. FIG. 5c illustrates an alternate embodiment of a distention valve 540 formed of a stiff material and containing an O-ring 560 to form a seal around the hysteroscope or another type of device that provides a transcervical pathway. The distention valve 540 may be formed of hard plastic and may have a screw-threaded portion 550 to be screwed on to a working channel of a hysteroscope or other device. The distention valves 500 and 540 illustrated in FIGS. 5a-5c may be fixed into place at any point on the sleeve 210 of the stabilization device 200 or may be movable along the sleeve 210 of the stabilization device 200.

FIG. 5d illustrates a kit 570 containing an intrafallopian contraceptive delivery device 580 and a stabilization device 200. The intrafallopian contraceptive delivery device may have a delivery catheter 581 and a control device 582 similar to the Essure device described above. The stabilization device 200 may have a sleeve 210 and a means for coupling the stabilization device to the control device 582 of the intrafallopian contraceptive delivery device. The stabilization device may alternately be any of the embodiments described above. The kit 570 may also include a hysteroscope such as the one illustrated in FIG. 6a. In another embodiment, the kit 570 may include a syringe loaded with a topical anesthetic. The syringe may have a first barrel and a second barrel, the first barrel loaded with the topical anesthetic and the second barrel loaded with a carrier. The topical anesthetic and the carrier may be mixed at the point of use with the use of a static mixer adapted to be coupled to the syringe. The static mixer may also be part of the kit 570.

In general, the current invention includes a method of coupling a stabilization device to a device that provides a transcervical pathway and coupling the stabilization device to a device for a minimally invasive gynecological procedure to stabilize the device for the minimally invasive gynecological procedure with respect to the device that provides the transcervical pathway. In one particular embodiment a control device of an intrafallopian contraceptive delivery device is stabilized with respect to a hysteroscope to fix the position of the fallopian tube insert within the fallopian tube. In this method, the delivery catheter of the intrafallopian contraceptive delivery device is inserted into a hysteroscope. The fallopian tube insert is then positioned within the fallopian tube for deployment. The position of the holding device with respect to the hysteroscope is then stabilized to fix the deployment position of the fallopian tube insert within the fallopian tube. The fallopian tube insert may then be deployed within the fallopian tube. The stabilization devices described above may be used to stabilize the position of the holding device with respect to the hysteroscope.

In an exemplary method of using the stabilization device 200, the stabilization device 200 is first coupled to the hysteroscope 600. The stabilization device 200 may be a sleeve 210 having a lumen and may be inserted into the working channel 620 of the hysteroscope 200 through a distention valve 610 that is attached to the end of the working channel 620 as illustrated in FIG. 6a. In this embodiment the distal end of the stabilization device 200 is inserted into the distention valve 610. The stabilization device 200 may be inserted into the distention valve 610 and the working channel 620 past a valve clamp 640. By inserting the sleeve 210 of the stabilization device 200 past the valve clamp 640 the valve clamp 640 may be used to couple the stabilization device 200 to the hysteroscope 200. Also, the sleeve 210 may be formed of a material that is hard enough not to be cut by the valve clamp 640 once it is clamped onto the sleeve 210. The valve clamp 640 may be a ball valve 630 as illustrated in FIG. 6c. Inserting the stabilization device 200 past the valve clamp 640 may also prevent the valve clamp 640 from snagging, pinching or cutting the delivery catheter and/or the guidewire of the intrafallopian contraceptive delivery device.

Markers may be placed on the outside of the sleeve 210 to indicate the depth to which the sleeve 210 should be inserted into the working channel 620. FIGS. 6a and 6b illustrate an embodiment where two markers 410, a distal marker 401 and a proximal marker 402, are on the outside of the sleeve 210. In this embodiment a first portion of the stabilization device 200 is inserted into the working channel 620 of the hysteroscope 600 until the distal marker 401 is entirely within the hysteroscope 600 and the proximal marker 402 is exposed immediately outside of the hysteroscope 600. In an alternate embodiment, there may be a single marker on the outside of the sleeve 210. In this embodiment, a first portion of the distal end of the sleeve 210 is inserted into the working channel 620 through the distention valve 610 until the marker is entirely within the hysteroscope 600, which in a particular embodiment may mean that the marker is entirely within the distention valve 610, and the proximal second portion of the stabilization device 200 remains outside of the hysteroscope 600.

Figure 6D:
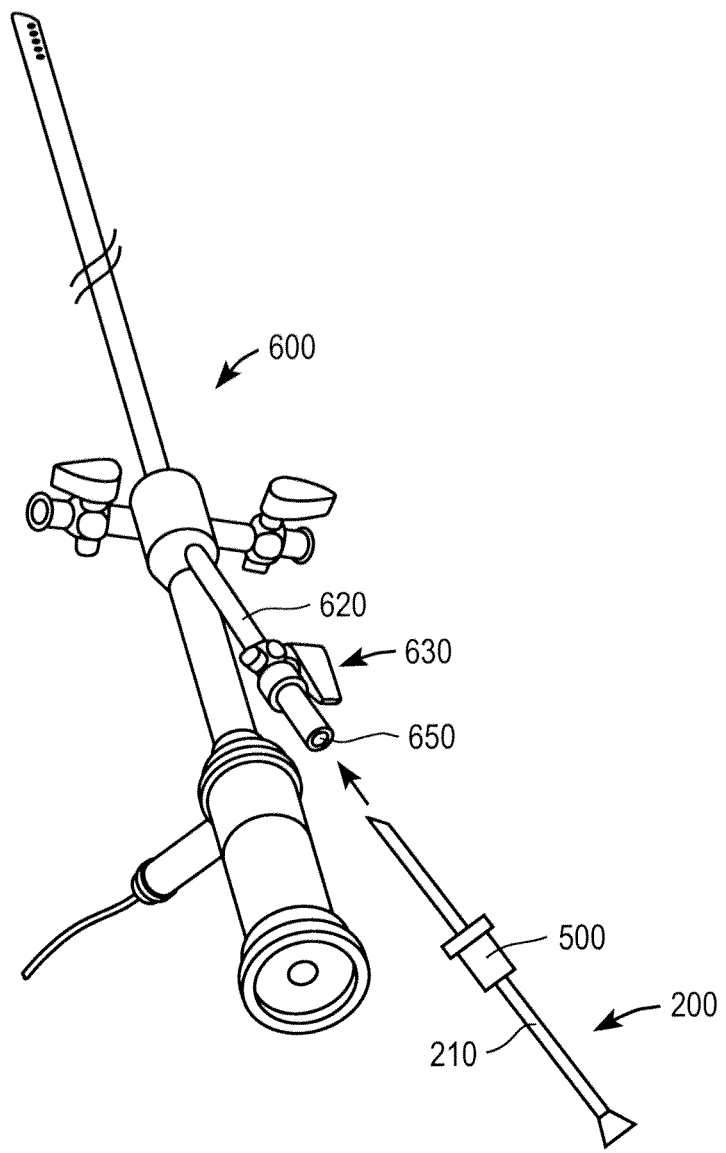
FIG. 6d illustrates a stabilization device having a distention valve positioned for insertion into the working channel of a hysteroscope.
Figure 6E:
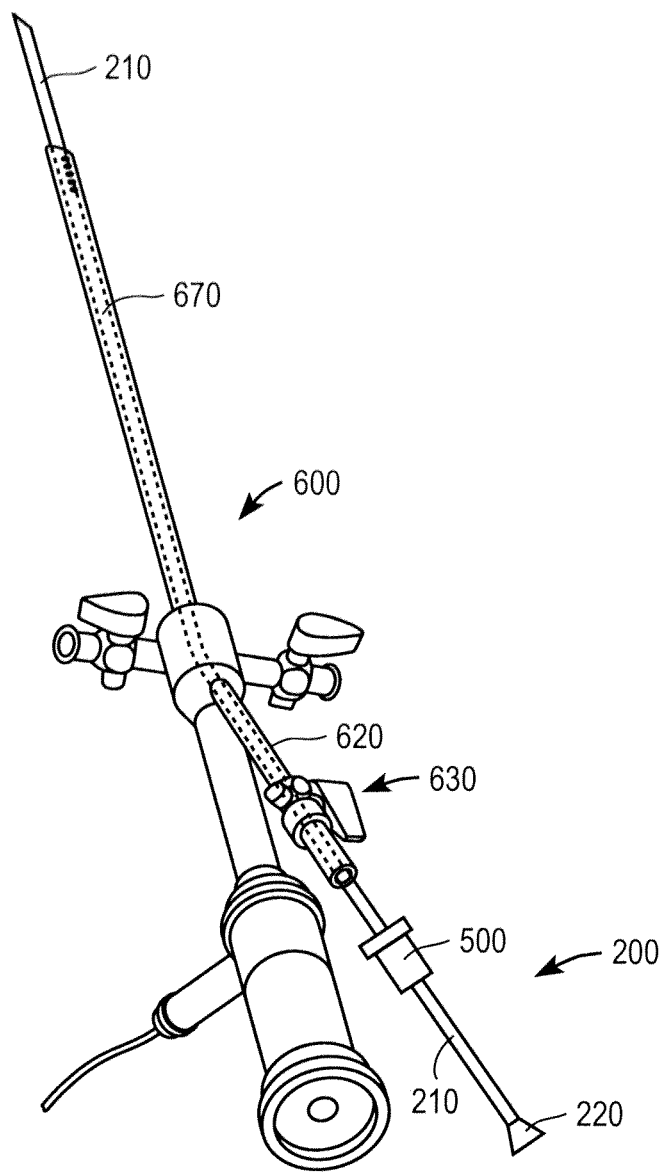
FIG. 6e illustrates a stabilization device having a distention valve and a length sufficient to reach beyond the end of the hysteroscope.

In another embodiment, the stabilization device 200 may be coupled to a distention valve 500, such as those illustrated in FIGS. 5a-5c and in FIG. 6d. In this embodiment, the stabilization device may be coupled to the hysteroscope 600 by coupling the distention valve 500 to the proximal end of the working channel 620 of the hysteroscope 600. As illustrated in FIG. 6d, the distention valve 500 coupled the stabilization device 200 may be coupled to the hysteroscope 600 after inserting the distal end of the sleeve 210 of the stabilization device 200 into the working channel 620 of the hysteroscope. The distention valve 500 may be a rubber-like material that may fit onto the proximal end of the working channel 620 to form a seal. The distention valve 500 may also be screwed onto the proximal end of a working channel 620 having a screw thread (not illustrated.) The distention valve 500 in this embodiment may be fixed in place on the sleeve 210, in which case the depth at which the sleeve 210 is inserted into the hysteroscope 600 is determined by where the distention valve 500 is positioned on the sleeve 210. In another embodiment, the distention valve 500 is movable along the sleeve 210 and the depth at which the sleeve 210 is inserted into the hysteroscope 600 may be adjusted. In one particular embodiment, the sleeve 210 of the stabilization device 200 may have a length such that the sleeve 210 extends beyond the tip of the channel 670 of the hysteroscope 600. The insertion of the distal end of the sleeve 210 into the hysteroscope 600 in this embodiment may be facilitated by the coupling of the distention valve 500 to the sleeve 210. In this embodiment, the length of the sleeve 210 may be sufficient to reach the fallopian tubes of a patient. In this embodiment the distal end of the sleeve 210 may be slightly curved or bendable to guide a delivery catheter of an intrafallopian contraceptive delivery device towards the opening of a fallopian tube. The stabilization device 200 may be further coupled to the hysteroscope 600 by clamping the valve clamp 630 onto the sleeve 210, as illustrated in FIGS. 6b and 6c.

Figure 6F:
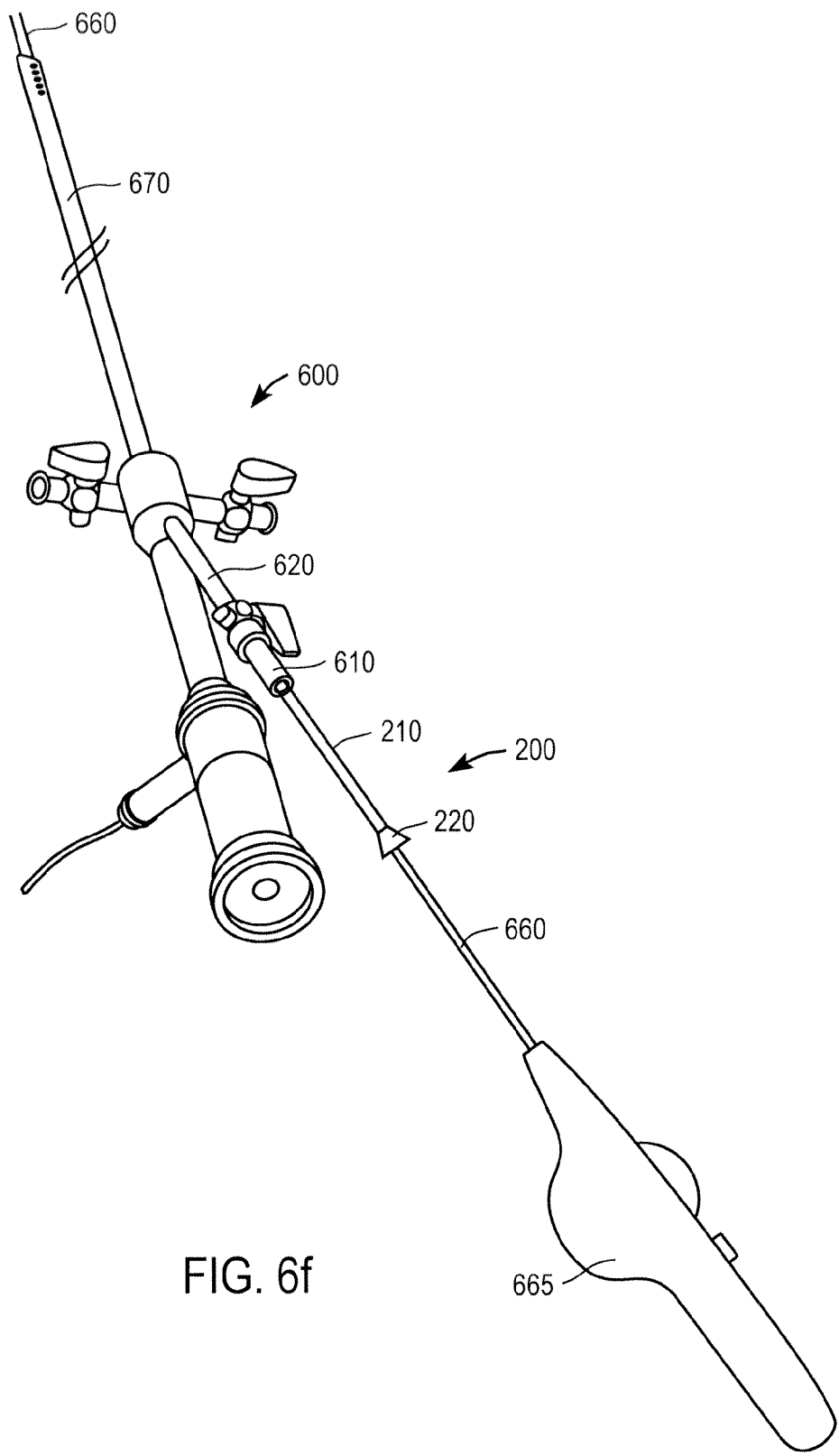
FIG. 6f illustrates a stabilization device inserted into a hysteroscope and a delivery catheter of an intrafallopian contraceptive delivery device inserted into the stabilization device and the hysteroscope.

As illustrated in FIG. 6f, an intrafallopian contraceptive delivery device is inserted into the lumen of the stabilization device and the hysteroscope 600. The intrafallopian contraceptive delivery device may be formed of a delivery catheter 660 coupled to a holding device 665. In this embodiment, the delivery catheter 660 is inserted into the sleeve 210 of the stabilization device 200 and into the hysteroscope 600 through the working channel 610 and the channel 670. The delivery catheter 660 contains a fallopian tube insert for deployment into a fallopian tube. After passing through the channel 670 of the hysteroscope 600, the delivery catheter 660 passes through the uterus and into one of the fallopian tubes where the delivery catheter 660 is positioned for deployment of the fallopian tube insert. Once the delivery catheter 660 is positioned for deployment of the fallopian tube insert, the operator of the intrafallopian contraceptive delivery device may verify the position of the fallopian tube insert before coupling the stabilization device 200 to the control device 665.

Figure 6G:
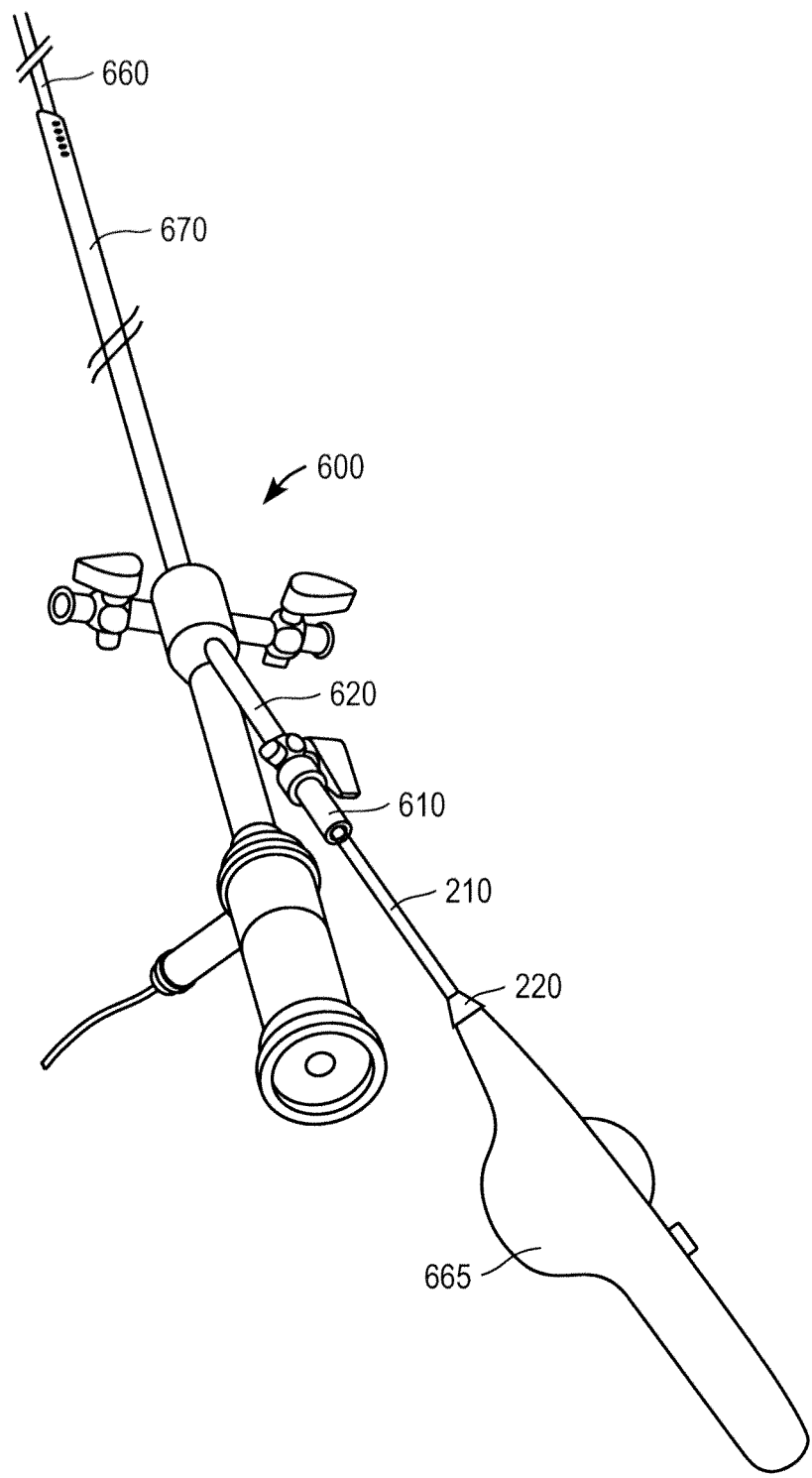
FIG. 6g illustrates a stabilization device coupled to both a hysteroscope and a control device of an intrafallopian contraceptive delivery device.

The stabilization device 200 may then be coupled to the holding device 665. FIG. 6g illustrates an embodiment where the stabilization device 200 is coupled to the holding device 665 mechanically by a mechanical fitting 210 that snaps onto the holding device 665. In an alternate embodiment the stabilization device 200 may be coupled to the holding device 665 by a friction fitting, such as those illustrated in FIGS. 3a-3c.

Figure 6H:
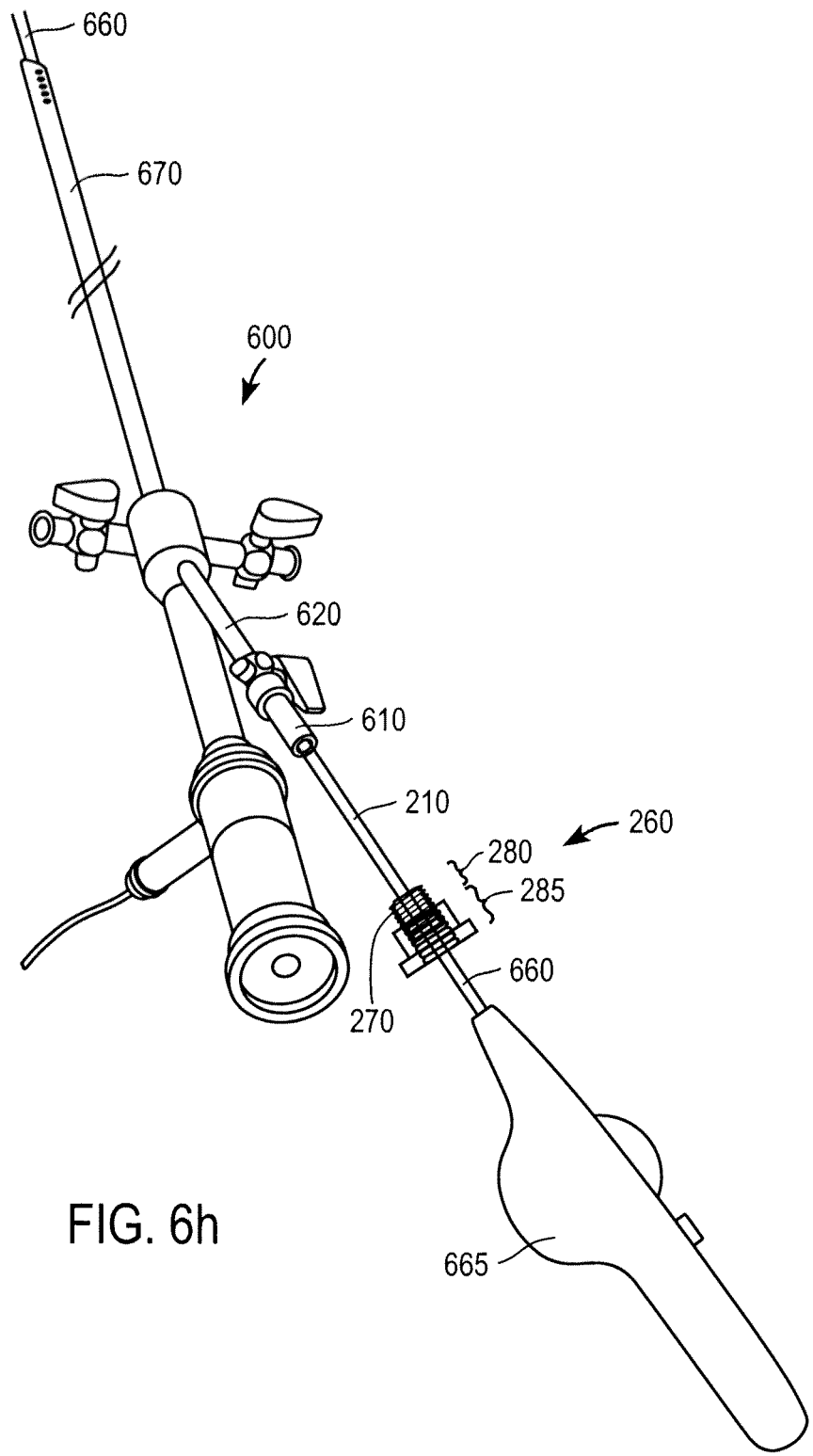
FIG. 6h illustrates a stabilization device coupled to the delivery catheter of an intrafallopian delivery device by an adjustable O-ring.

In another embodiment, the stabilization device 200 may be coupled to the intrafallopian contraceptive device by coupling the stabilization device 200 to the delivery catheter 660. An example of this embodiment is illustrated in FIG. 6h. FIG. 6h illustrates a stabilization device 200 having an adjustable O-ring 260 at the proximal end. The inner diameter of the O-ring 270 may be tightened around the delivery catheter 660 by screwing the second sleeve 285 of the adjustable O-ring 260 onto the first sleeve 280 of the adjustable O-ring. The stabilization device 200 may also be coupled to the delivery catheter 660 by a simple O-ring having an inner diameter sufficient to form a seal around the delivery catheter 660. The adjustable O-ring 260 or a single O-ring may be formed in combination with a duckbill valve.

Figure 6I:
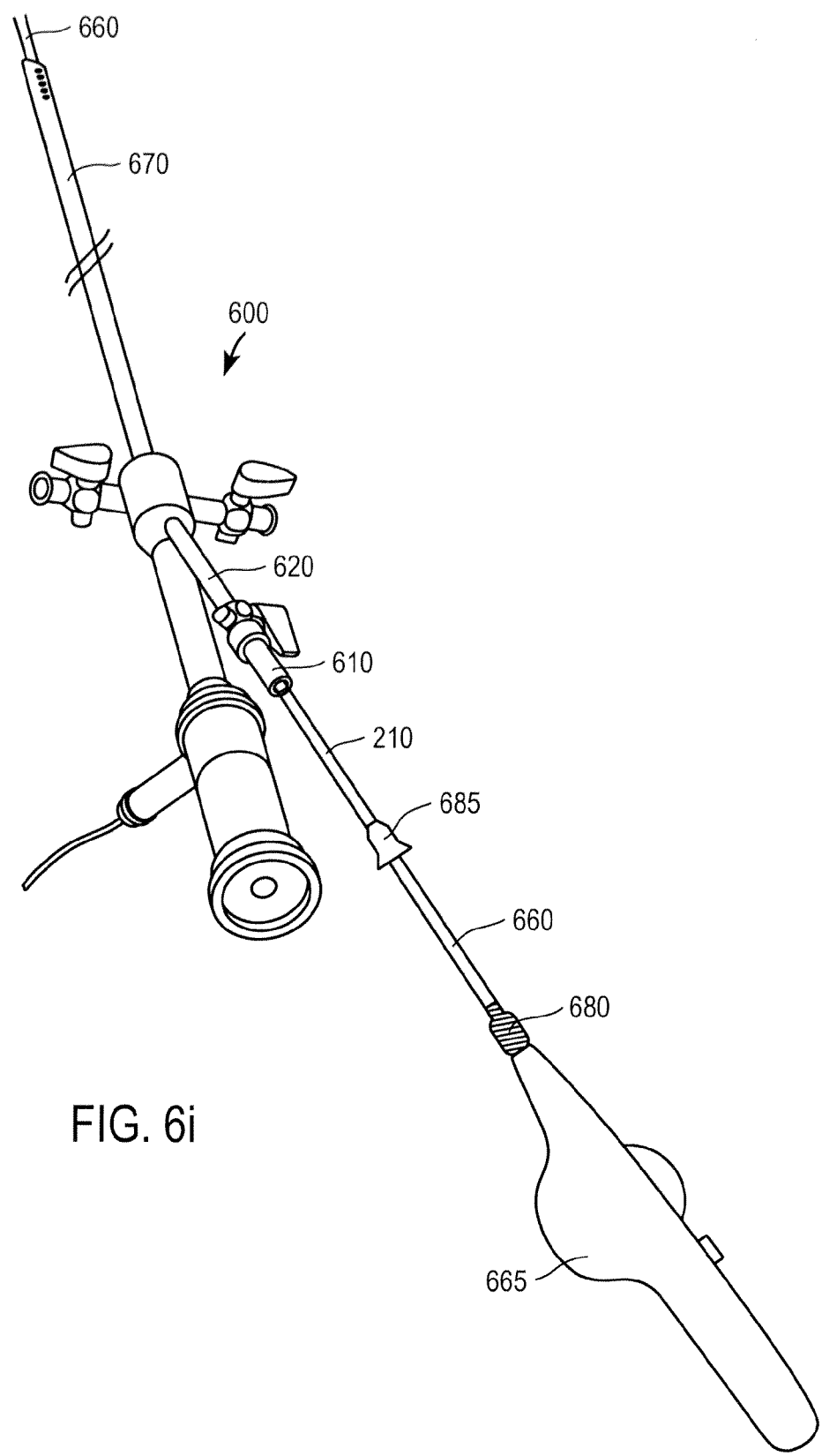
FIG. 6i illustrates a stabilization device having a mechanical fitting designed to couple to an adaptor on the end of the control device of an intrafallopian contraceptive delivery device.
Figure 6J:
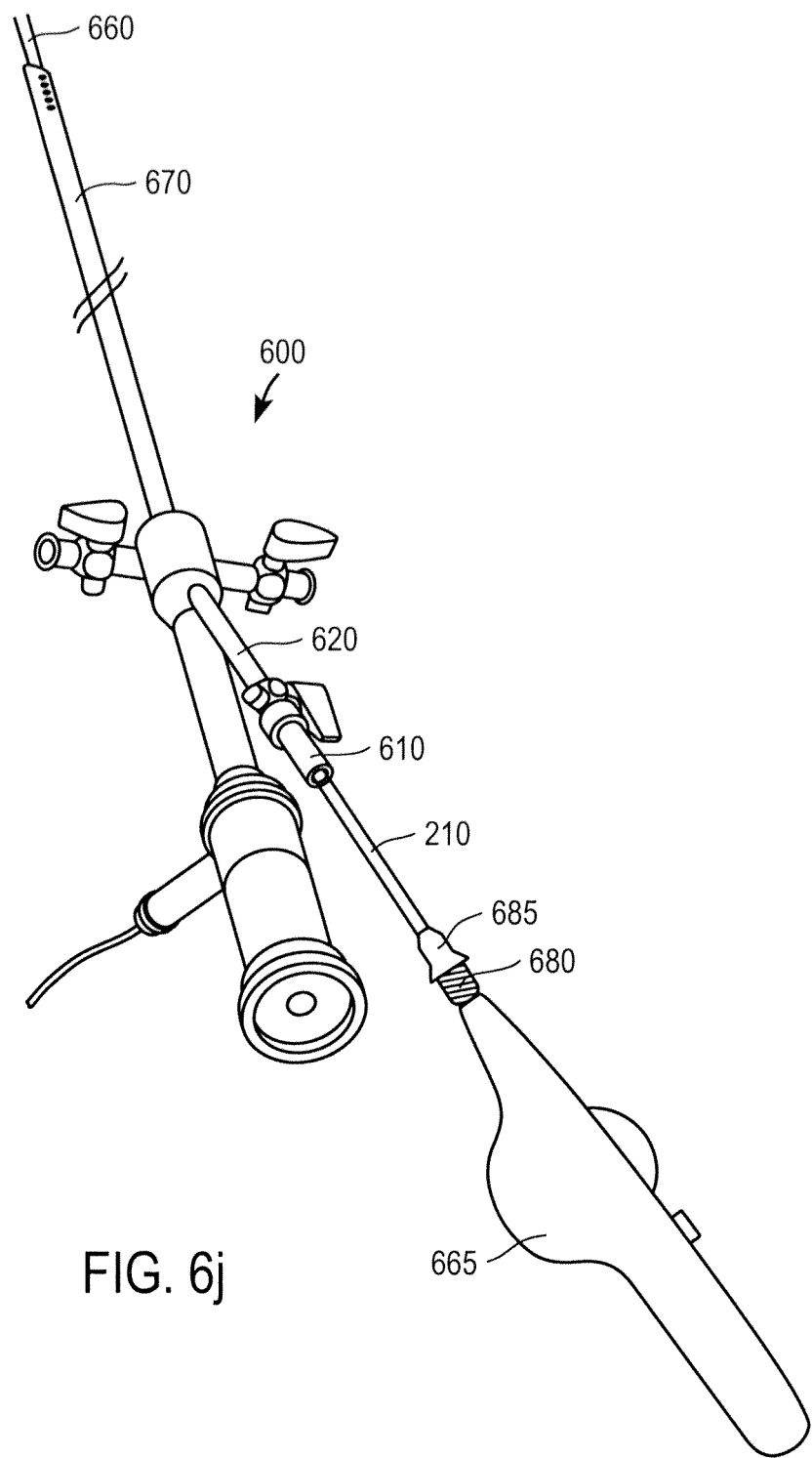
FIG. 6j illustrates the stabilization device of FIG. 6h coupled to the adaptor on the end of the control device of the intrafallopian contraceptive delivery device.

FIG. 6i illustrates another embodiment of a stabilization device 200 that may be coupled to the control device 665 of the intrafallopian contraceptive delivery device by a mechanical fitting. In this embodiment the mechanical fitting 685 is designed to mechanically fit onto an adaptor 680 that is coupled to the intrafallopian contraceptive delivery device. The adaptor 680 may be coupled to the control device 665 or to the delivery catheter 660. After positioning the intrafallopian contraceptive delivery device to deploy a fallopian tube insert the stabilization device 200 may be coupled to the intrafallopian contraceptive delivery device by mechanically fitting the mechanical fitting 685 to the adaptor 680.

In yet another embodiment, the stabilization device 200 may be pre-coupled to the intrafallopian contraceptive delivery device. In this embodiment it would not be necessary to couple the stabilization device 200 to the intrafallopian contraceptive delivery device.

The position of the fallopian tube insert for deployment from the delivery catheter 660 may be verified and adjusted again before coupling or re-coupling the stabilization device 200 to the hysteroscope 600. In one embodiment, the verification and potential adjustment of the position of the fallopian tube insert for deployment may be performed prior to clamping the valve clamp 630 onto the sleeve 210 of the stabilization device 200. In one embodiment, the positioning of the fallopian tube insert for deployment may be adjusted after coupling the stabilization device to the intrafallopian contraceptive delivery device by using a feed-forward mechanism of the intrafallopian contraceptive delivery device. FIGS. 6k-6m illustrate this embodiment with a cut-away side view of the control device 665 of an intrafallopian contraceptive delivery device. In FIG. 6k the distal tip of the intrafallopian contraceptive delivery device is at a first position beyond the ostium 675 within a fallopian tube and the stabilization sheath 200 is coupled to the adapter 680 by the mechanical fitting 685. In FIG. 6l, a user of the control device 665 may then roll back the thumbwheel 667 of the control device 665 to mechanically fit the adapter 680 to the control device mechanical fitting 687 and to feed-forward the core wire 671.

In an embodiment, the core wire 671 is moved forward into the fallopian tube by approximately 1.6 cm to compensate for user error. In FIG. 6m, rolling back the thumbwheel 667 will break away a portion 672 of the sheath 673 that contains the delivery catheter 660. After the portion 672 of the sheath 673 breaks away inside of the control device 665, the delivery catheter 660 is retracted to uncover the core wire 671 to expose the fallopian tube insert (not shown) that is wound down over the core wire 671.

The position of the delivery catheter 660 for the deployment of the fallopian tube insert may be verified by fluoroscopy, ultrasound (including hysterosalpingo-contrast-ultrasonography (HyCoSy) and stimulated acoustic emission (SAE-HyCoSy)), radiography, or visual orientation using a camera placed through the hysteroscope 600. In one embodiment the distal end of the delivery catheter 660 or the distal end of a stabilization device 200 having a length sufficient to reach the fallopian tubes may be marked with a radiopaque material that may be viewed by radiography. In this embodiment the positioning and verification of the position of the delivery catheter 660 for the deployment of the fallopian tube insert may be done by viewing the radiopaque mark on either the delivery catheter 20 or on the distal end of the stabilization device 200.

Alternatively, the uterus may be distended using a contrast media that is visible by either ultrasound or radiography for the positioning and verification of the position of the delivery catheter 660 for the deployment of the fallopian tube insert. In one embodiment, the contrast media may be a fluid or gel containing microbubbles that are a shell filled with a contrast agent such as a gas or other ultrasound contrast enhancing agent viewable by ultrasound such as perfluorocarbon-exposed sonicated dextrose albumin microbubbles. In an embodiment, the microbubbles may contain a topical anesthetic such as lidocaine that may be delivered to the uterine cavity by applying ultrasound at an energy sufficient to cause the microbubbles to burst and release the anesthetic. In one exemplary method, the positioning of the stabilization sheath 200 or the delivery catheter 600 may be accomplished using ultrasound to view the contrast media within the microbubbles. The microbubbles may then be burst by changing the ultrasound energy to release the anesthetic into the uterine cavity. The release of the anesthetic from the microbubbles may be monitored and regulated by measuring the harmonic response to the ultrasound energy. In another embodiment the anesthetic may be released from some of the microbubbles prior to the performance of the minimally invasive gynecological procedure to an extent that would anesthetize the tissues surrounding the uterine cavity but to still have microbubbles remaining for ultrasound positioning of the device for the minimally invasive gynecological procedure.

FIGS. 7a-7d illustrate an alternate embodiment where the device that provides the transcervical pathway is an access catheter. In this embodiment the access catheter has a balloon to form a seal between the access catheter and the cervix and to fix the position of the access catheter during a minimally invasive gynecological procedure. FIG. 7a illustrates a cut-away side view of the access catheter 700 having a tubular catheter body 710 that includes a distal end 712 and a proximal end 714 and a lumen 715. The lumen 715 provides a transcervical pathway to access the uterine cavity with a surgical instrument. An elongated inflatable balloon 720 (illustrated in the deflated state) is sealingly affixed to and encloses a distal portion of the catheter body 710. The balloon 720 contains a fixed residual volume of fluid which is displaced by operation of the fluid displacement sleeve 730. FIG. 7b illustrates the outer surface of the access catheter 700. FIG. 7c illustrates the balloon 720 of the access catheter 700 once it is placed within the os of the cervix.

The displacement sleeve 730 may then be slid along the outside of the catheter 710 towards the distal end 712 of the tubular catheter body 710 to displace the fixed residual volume of fluid into the portion of the balloon 720 that is within the os of the cervix. FIG. 7d illustrates the expanded balloon 720 in the cervix region after the displacement sleeve 730 has been slid towards the distal end 712 of the tubular catheter body 710. The expanded balloon 720 serves to hold the access catheter 700 in place during a minimally invasive gynecological procedure such as the use of an intrafallopian contraceptive delivery device to place fallopian tube inserts within the fallopian tubes.

Similar to the use of the stabilization sheath 200 with the hysteroscope 600, the stabilization sheath 200 may be coupled to the end of the access catheter 700 to provide a pathway for a device for a nonsurgical gynecological procedure and to provide a means for coupling the stabilization device to the device for the nonsurgical gynecological procedure. The stabilization device 200 may be coupled to the access catheter 700 by a distention valve 500 that has formed a seal by friction fitting with the tubular catheter body 710. The stabilization device 200 may be coupled to the tubular catheter body 710 by other means such as an O-ring, and adjustable O-ring, or a screw thread. The stabilization device 200 also has a means for coupling the stabilization device 200 to the device for a minimally invasive gynecological procedure such as a mechanical fitting 220 or any of the other embodiments described above in relation to the hysteroscope embodiment. The stabilization device 200 may also have a port 470. Any of the methods described above in relation to the hysteroscope embodiment may be applied to the use of the access catheter 700 in place of the hysteroscope. The stabilization device 200 may be valuable for use with the access catheter because it provides a stable fixed longitudinal distance between the device for the minimally invasive gynecological procedure and the access catheter during the gynecological procedure. This may significantly improve the accuracy of the gynecological procedure. For example, the accuracy of placement of fallopian tube inserts from an intrafallopian contraceptive delivery device may be improved.

Figure 8A:
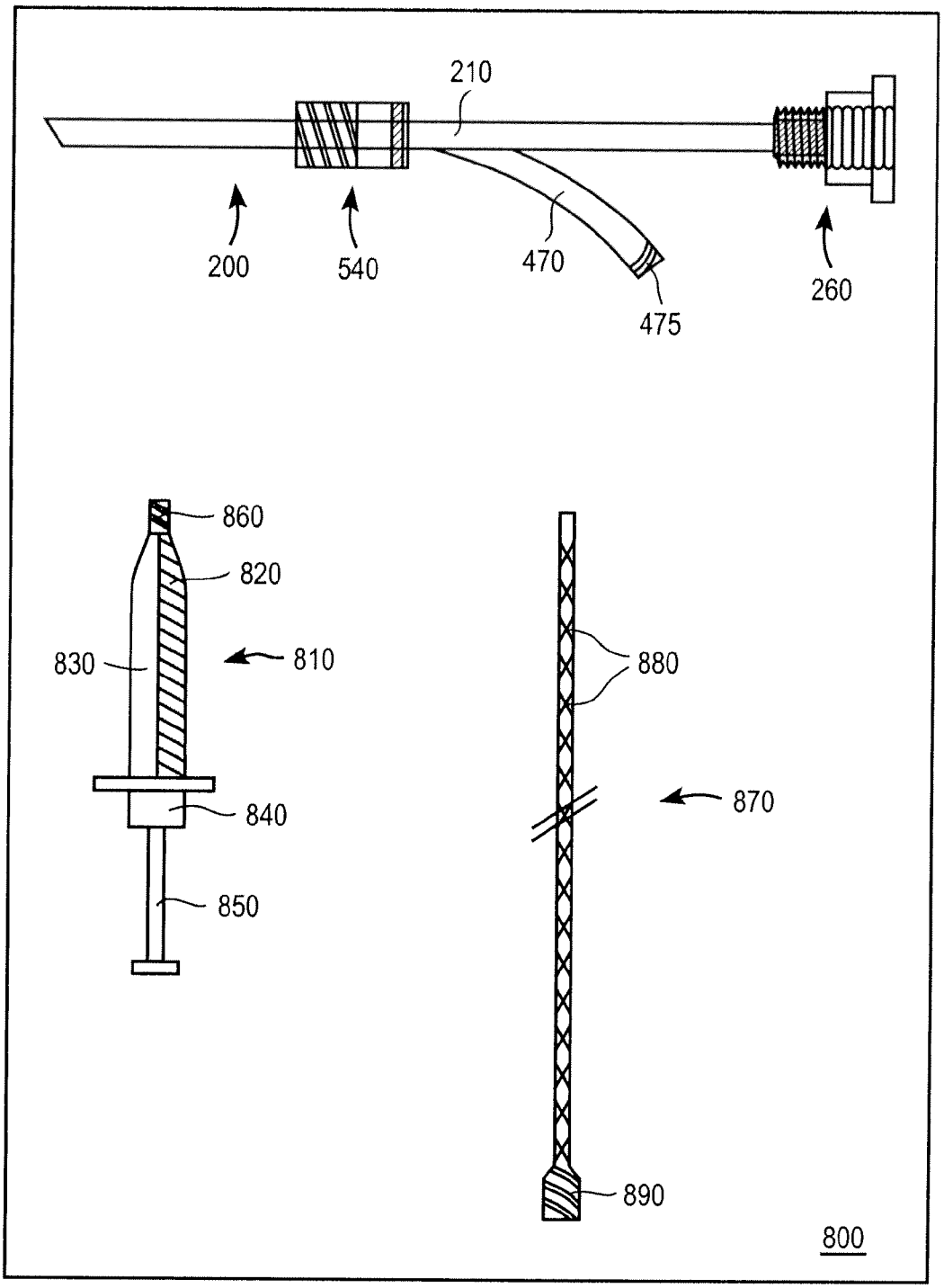
FIG. 8a illustrates a kit containing a stabilization device having a port for an anesthetic delivery catheter, an anesthetic delivery catheter that has static mixer capabilities, and a dual-barrel syringe.

In another embodiment, prior to a minimally invasive gynecological procedure, a topical anesthetic may be applied to the uterus. In a method of a minimally invasive procedure of placing fallopian tube inserts into the fallopian tubes the topical anesthetic may be applied to a region around the opening of the fallopian tubes (the ostium). The topical anesthetic may be delivered to the uterus using a port on a stabilization device. FIG. 8a illustrates a kit 800 containing a stabilization device 200 having a port 470, a syringe 810, and an anesthetic delivery catheter 870. The stabilization device 200 having a port 470 may be in the form of any of the embodiments discussed above. In the embodiment illustrated in FIG. 8a the stabilization device 200 is formed of a sleeve 210 to which a distention valve such as 540 may be coupled and to which an adjustable O-ring 260 may be coupled. The port 475 may also include a screw thread at the proximal end to screw the syringe 810 to the port 470. The syringe 810 may be a single-barreled syringe or a dual-barreled syringe as illustrated in FIG. 8a. A single-barreled syringe may be pre-loaded with an anesthetic mixture or may be filled by a physician performing a gynecological procedure.

The anesthetic mixture may by an anesthetic such as lidocaine hydrochloride and may have a concentration in the range of 0.5% and 15%, and more particularly in the range of 5% and 10%. In an alternate embodiment, the topical anesthetic may be a mixture of an amide anesthetic such as lidocaine, lignocaine, marcaine, or carbocaine, a buffering agent to bring the pH of the mixture to at least 5.5, optionally a viscosity agent and/or a solubilising agent. In an embodiment, the viscosity agent is present in an amount sufficient to give the topical anesthetic a viscosity greater than water and to maintain viscosity at body temperature. In one particular embodiment, the viscosity agent may be hydroxypropyl methylcellulose. The solubilizing agent serves to inhibit crystallization and therefore also the precipitation of the anesthetic compounds within the topical anesthetic mixture. An example of a solubilizing agent that may be used in the formulation is N-methyl-2-pyrrolidone. The solubilizing agent enables the solution to hold a higher concentration of the anesthetic agent and thereby increases the bio-availability, potency, and effect of the anesthetic agent. Additionally, the topical anesthetic may contain materials that enhance the absorption of the anesthetic into a patient's tissues.

The topical anesthetic may be mixed at a point of use to further prevent the precipitation of the anesthetic agent before application and to prolong the shelf-life of the anesthetic agent. The potency of the topical anesthetic may decrease once the anesthetic agent is mixed with a carrier material, therefore point of use mixing ensures that the topical anesthetic applied to the uterus and the fallopian tubes is potent.

A dual-barreled syringe 810 may be used to mix the topical anesthetic at the point of use. The dual-barreled syringe has a first barrel 820 to contain a topical anesthetic such as lidocaine hydrochloride. The topical anesthetic within the first barrel 820 may have a concentration in the range of 2% and 15% anesthetic, and more particularly may have a concentration of approximately 12%. The topical anesthetic may be a liquid, a paste, or a gel. The second barrel 830 may contain a carrier material that will be mixed with the topical anesthetic from the first barrel 820. In an embodiment, the carrier material may be a buffer agent or a buffer agent in combination with a solubilizing agent and a viscosity agent. The topical anesthetic may further contain materials that prolong the shelf-life of the anesthetic if the syringe is pre-loaded.

The syringe 810 also has a plunger 850 and a tip 860 that may have a screw thread for attachment to the anesthetic delivery catheter 890 or the port 470. The syringe 810 may also include a lock 840 to prevent the leakage of the contents of the syringe if pre-loaded.

The kit 800 may also include an anesthetic delivery catheter 870. The anesthetic delivery catheter 870 may have a length sufficient to apply the topical anesthetic mixture to any portion of a uterus or a cervix. In an embodiment, the length of the anesthetic delivery catheter is a length sufficient to apply the topical anesthetic mixture to the region in the uterus around the fallopian tubes. The anesthetic delivery catheter 870 may also have static mixing portions 880 to mix the contents of a dual barrel syringe at the point of use as the topical anesthetic and the carrier are mixed. The static mixer portions 880 may extend the entire length of the anesthetic delivery catheter 870 or may extend for only the length necessary to sufficiently mix the topical anesthetic with the carrier. The anesthetic delivery catheter 870 may also be an ordinary catheter without static mixing capabilities. The anesthetic delivery catheter 890 may have a screw thread at the proximal end for coupling with the syringe 810 or with the proximal end of the port 470 after insertion of the anesthetic delivery catheter into the port 470. A biocompatible polymer may be used to form the anesthetic delivery catheter 870 and may be flexible. The anesthetic delivery catheter 870 may be reusable or disposable.

The kit 800 may also include a static mixing tip (not illustrated). The proximal end of the static mixing tip may be coupled to the tip 860 of the syringe 810. The length of the static mixing tip depends on the amount of mixing necessary to sufficiently mix a topical anesthetic with a carrier. The distal end of the static mixing tip may be coupled to and anesthetic delivery catheter 870 and/or to the port 470.

Figure 8B:
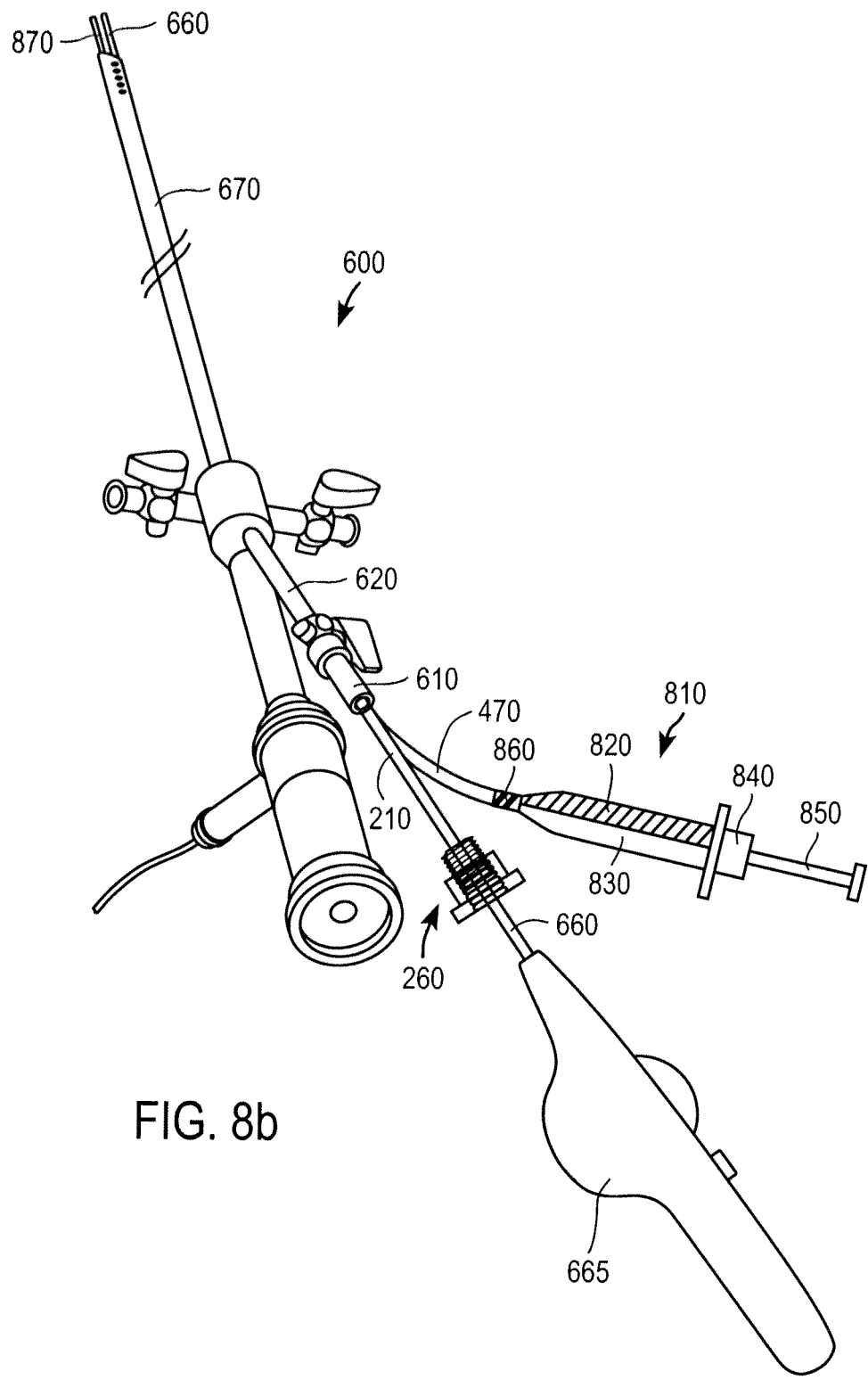
FIG. 8b illustrates a stabilization device having a port for an anesthetic delivery catheter coupled to a syringe containing an anesthetic and anesthetic carrier.

FIG. 8b illustrates the use of the components of the kit 800 with a hysteroscope 600. The components of the kit 800 and the different embodiments of the components of the kit 800 may also be used with an access catheter 700 such as the one illustrated in FIGS. 7a-7d. A stabilization device 200 having a port 470 into which the anesthetic delivery catheter has been inserted and to which a syringe 810 has been coupled is illustrated. The topical anesthetic may be applied to the uterus or cervix before inserting the delivery catheter 660 for the intrafallopian contraceptive device into the stabilization device 200 and the hysterscope 600.

In an embodiment, the topical anesthetic may be a mixed with a carrier at the point of use using a static mixer within the anesthetic delivery catheter 870 once the topical anesthetic in the first barrel 820 and the carrier in the second barrel 830 of the dual barrel syringe 810 are injected into the anesthetic delivery catheter 870 by unlocking the lock 840 and depressing the plunger 850. The syringe 810 may have been pre-loaded or may be loaded at the point of use. The anesthetic delivery catheter may be positioned to deliver the topical anesthetic to a particular region of the uterus or cervix by ultrasound or radiography, as well as by visual orientation using a camera in a hysteroscope. To position the anesthetic delivery catheter by radiography, the tip of the anesthetic delivery catheter may have a radiographic marker at the distal end. Alternatively, the uterus may be distended with a contrast media for ultrasound or radiography prior to the application of the topical anesthetic. The minimally-invasive gynecological procedure may be performed between 2 minutes to 24 hours after the application of the topical anesthetic. The topical anesthetic may need a few minutes to take effect. In one particular embodiment, the minimally-invasive gynecological procedure may be performed within the approximate range of 5 minutes and 20 minutes after the application of the topical anesthetic.

Once the delivery catheter of the intrafallopian contraceptive delivery device is positioned to deploy the fallopian tube insert the fallopian tube insert is deployed into the fallopian tube. In an embodiment, the fallopian tube insert may have the general structure of a metal frame formed from a metal such as stainless steel or superelastic or shape memory material. The frame may be expanded radially from a first diameter to a second diameter that is larger than the first diameter. The insert may expand in a way that causes it to resiliently apply an anchoring force against the wall of the fallopian tube. The surface of the insert may be designed to facilitate epithelial growth; one way of doing this is to provide the insert with and open or lattice-like framework to promote and support epithelial growth into as well as around the insert to ensure secure attachment to an embodiment within the wall of the body lumen. The hollow inner portion within the frame may include a tissue ingrowth agent such as a polyester fiber or other materials known to facilitate fibrotic or epithelial growth. The surface of the frame may also be modified or treated or include such a tissue ingrowth material.

In other embodiments, the device may be coated or seeded to spur epithelialization. For example, the device can be coated with a polymer having impregnated therein a drug, enzyme or protein for inducing or promoting epithelial tissue growth. Once a fallopian tube insert has been placed into one fallopian tube the methods described above may be repeated to place a fallopian tube insert into the second fallopian tube. This may be done with the same delivery catheter 660 if the delivery catheter 660 contains two fallopian tube inserts in series or in parallel within a delivery catheter that has two lumens. Alternatively the second fallopian tube insert may be inserted with a second intrafallopian contraceptive delivery device.

Figure 9:
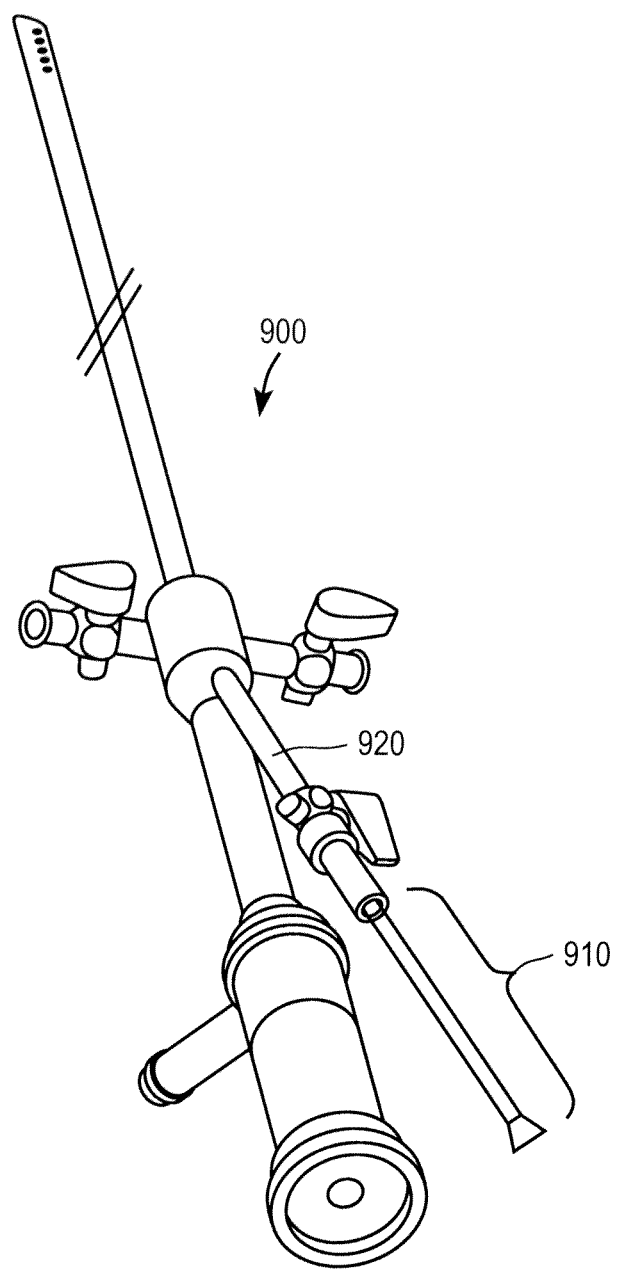
FIG. 9 illustrates a stabilization device permanently coupled to a hysteroscope.

In an alternate embodiment, illustrated in FIG. 9, the stabilization device 910 may be permanently coupled to a hysteroscope 900. The stabilization device 910 may be coupled to the working channel 920 as an integrated part.

Figure 10:
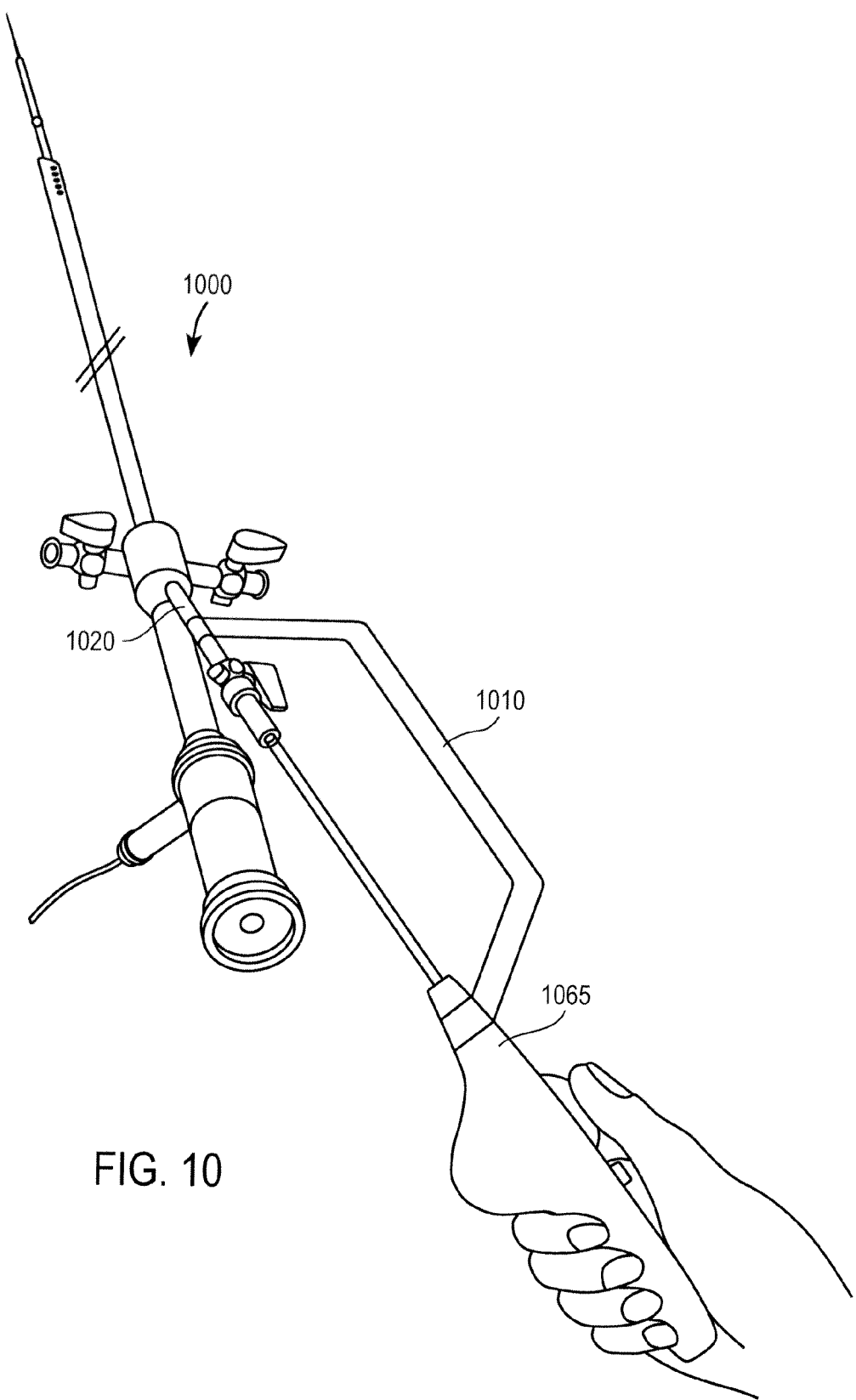
FIG. 10 illustrates an embodiment of a stabilization device shaped like an arm.

In another embodiment, the stabilization device may be an arm. FIG. 10 illustrates one example of this embodiment where the stabilization device is an arm 1010 that is coupled to the hysteroscope 1000 and the handle of the control device 1065 to create a fixed distance between the hysteroscope 1000 and the control device 1065. In this particular embodiment, the stabilization device shaped like an arm is coupled to the working channel 1020 and to the front portion of the handle of the control device 1065. The stabilization device 1010 shaped like an arm may be coupled to the hysteroscope 1000 and to the control device 1065 at other various points sufficient to fix the position of the hysteroscope 1000 with respect to the control device 1065.

While the exemplary embodiment of the present invention has been described in some detail for clarity of understanding and by way of example, a variety of adaptations, changes and modifications will be obvious to those who are skilled in the art. Hence the scope of the present invention is limited solely by the following claims.

We claim:

1. A stabilization device, comprising:
   a sleeve having a lumen extending between a proximal end and a distal end of the sleeve, the sleeve adapted to be inserted into a working channel of a hysteroscope;
   a proximal seal at the proximal end of the sleeve through which a catheter can be advanced into the lumen and into the working channel of the hysteroscope, wherein the proximal seal comprises a duckbill valve; and
   a distention valve fixed in place on the sleeve such that the distention valve is not movable along the sleeve, the distal end of the sleeve extends distally beyond the distention valve and a depth at which the distal end of the sleeve can be inserted into the working channel of the hysteroscope is determined by where the distention valve is fixed in place on the sleeve, wherein the distention valve includes a portion adapted to fit onto and form a seal around the working channel of the hysteroscope.

2. The stabilization device of claim 1, wherein the proximal seal comprises an O-ring.

3. The stabilization device of claim 1, wherein the proximal seal comprises a membrane.

4. The stabilization device of claim 1, wherein the proximal seal comprises a double membrane.

5. The stabilization device of claim 1, wherein the proximal seal comprises a hole seal.

6. The stabilization device of claim 1, wherein the distention valve is adjacent the proximal seal at the proximal end of the sleeve.

7. The stabilization device of claim 1, wherein the sleeve is sized and dimensioned to extend past a valve clamp of the working channel when the distention valve is fitted onto the working channel.

8. The stabilization device of claim 1, wherein the proximal seal is adapted to prevent backflow of fluid out of the stabilization device.

9. The stabilization device of claim 8, wherein the proximal seal is adapted to prevent backflow of fluid out of the stabilization device when the catheter is advanced into the lumen and into the working channel of the hysteroscope.

10. The stabilization device of claim 1, wherein the distal end of the sleeve is tapered.

11. The stabilization device of claim 1, wherein the distention valve is permanently fixed in place on the sleeve.

12. A kit, comprising:
    a catheter for an intrafallopian contraceptive procedure; and
    a stabilization device comprising:
       a sleeve having a lumen extending longitudinally between a proximal end and a distal end of the sleeve, the sleeve adapted to be inserted into a working channel of a hysteroscope;
       a proximal seal at the proximal end of the sleeve through which a catheter can be advanced into the lumen and into the working channel of the hysteroscope, wherein the proximal seal comprises a duckbill valve; and
       a distention valve fixed in place on the sleeve such that the distention valve is not movable along the sleeve, the distal end of the sleeve extends distally beyond the distention valve and a depth at which the distal end of the sleeve can be inserted into the working channel of the hysteroscope is determined by where the distention valve is fixed in place on the sleeve, wherein the distention valve includes a portion adapted to fit onto and form a seal around the working channel of the hysteroscope.

13. The kit of claim 12, wherein the proximal seal comprises an O-ring.

14. The kit of claim 12, wherein the proximal seal comprises a membrane.

15. The kit of claim 12, wherein the proximal seal comprises a double membrane.

16. The kit of claim 12, wherein the proximal seal comprises a hole seal.

17. The stabilization device of claim 12, wherein the proximal seal is adapted to prevent backflow of fluid out of the stabilization device.

18. The stabilization device of claim 17, wherein the proximal seal is adapted to prevent backflow of fluid out of the stabilization device when the catheter is advanced into the lumen and into the working channel of the hysteroscope.

19. The kit of claim 12, wherein the distention valve is adjacent the proximal seal at the proximal end of the sleeve.

20. The kit of claim 12, wherein the sleeve is sized and dimensioned to extend past a valve clamp of the working channel when the distention valve is fitted onto the working channel.

21. The kit of claim 12, wherein the distal end of the sleeve is tapered.

22. The kit of claim 12, wherein the distention valve is permanently fixed in place on the sleeve.

* * * * *